US012778783B2

(12) United States Patent
Myers

(10) Patent No.: US 12,778,783 B2
(45) Date of Patent: Nov. 3, 2026

(54) URINE COLLECTION SYSTEM INCLUDING A SIZING DEVICE

(71) Applicant: PureWick Corporation, El Cajon, CA (US)

(72) Inventor: Benjamin Myers, Atlanta, GA (US)

(73) Assignee: PUREWICK CORPORATION, Covington, GA (US)

( * ) Notice: Subject to any disclaimer, the term of this patent is extended or adjusted under 35 U.S.C. 154(b) by 749 days.

(21) Appl. No.: 17/758,152

(22) PCT Filed: Dec. 30, 2020

(86) PCT No.: PCT/US2020/067451
§ 371 (c)(1),
(2) Date: Jun. 29, 2022

(87) PCT Pub. No.: WO2021/138411
PCT Pub. Date: Jul. 8, 2021

(65) Prior Publication Data

US 2023/0028575 A1 Jan. 26, 2023

Related U.S. Application Data

(60) Provisional application No. 62/956,767, filed on Jan. 3, 2020.

(51) Int. Cl.
*A61F 5/44* (2006.01)
*A61F 5/451* (2006.01)

(52) U.S. Cl.
CPC ............ *A61F 5/4404* (2013.01); *A61F 5/451* (2013.01)

(58) Field of Classification Search
CPC .... A61F 13/4758; A61F 5/455; A61F 5/4408; A61F 5/453; A61F 5/4404;
(Continued)

(56) References Cited

U.S. PATENT DOCUMENTS

| | | | |
|---|---|---|---|
| 670,602 | A | 3/1901 | Baker |
| 737,443 | A | 8/1903 | Mooers |

(Continued)

FOREIGN PATENT DOCUMENTS

| | | | |
|---|---|---|---|
| AU | 2018216821 | A1 | 8/2019 |
| AU | 2021299304 | A1 | 2/2023 |

(Continued)

OTHER PUBLICATIONS

US 9,908,683 B2, 03/2018, Sandhausen et al. (withdrawn)

(Continued)

*Primary Examiner* — Leslie R Deak
*Assistant Examiner* — Linnae E. Raymond
(74) *Attorney, Agent, or Firm* — Ballard Spahr LLP

(57) ABSTRACT

Examples relate to devices, systems, and methods for fluid collection such as urine. A urine collection system (100) includes a urine collection device (102) and a sizing device (150) secured or securable to the urine collection device (100). The sizing device (150) includes a body (152) and a recess (185). The body (152) has a distal end (160) and an attachment end (155) distal to the distal end (160). The attachment end (155) defines an opening (180), and the recess (185) extends into the body (152) from the opening (180). The recess (185) is sized and dimensioned to receive a portion of the urine collection device (102) and secure the sizing device (150) to the urine collection device (102).

20 Claims, 5 Drawing Sheets

(58) Field of Classification Search
CPC ...... A61F 5/44–443; A61F 5/451–4556; A61F 5/449; A61F 13/47272; A61M 2210/1092
See application file for complete search history.

(56) References Cited

U.S. PATENT DOCUMENTS 1,015,905 A 1/1912 Northrop
1,032,841 A 7/1912 Koenig
1,178,644 A 4/1916 Johnson
1,387,726 A 8/1921 Karge
1,742,080 A 12/1929 Jones
1,979,899 A 11/1934 Obrien et al.
2,241,010 A 5/1941 Chipley
2,262,772 A 11/1941 Peder
2,326,881 A 8/1943 Packer
2,379,346 A 6/1945 Farrell
2,485,555 A 10/1949 Bester
2,571,357 A 10/1951 Charles
2,613,670 A 10/1952 Edward
2,616,426 A 11/1952 Adele
2,644,234 A 7/1953 Earl
2,648,335 A 8/1953 Chambers
2,789,560 A 4/1957 Weimer
2,859,786 A 11/1958 Tupper
2,944,551 A 7/1960 Carl
2,968,046 A 1/1961 Duke
2,971,512 A 2/1961 Reinhardt
3,032,038 A 5/1962 Swinn
3,077,883 A 2/1963 Hill
3,087,938 A 4/1963 Hans et al.
3,114,916 A 12/1963 Hadley
3,169,528 A 2/1965 Knox et al.
3,171,506 A 3/1965 Therkel
3,175,719 A 3/1965 Herndon
3,194,238 A 7/1965 Breece
3,198,994 A 8/1965 Hildebrandt et al.
3,221,742 A 12/1965 Egon
3,312,221 A 4/1967 Overment
3,312,981 A 4/1967 Mcguire et al.
3,340,876 A * 9/1967 Hill ......................... A61F 5/451 600/580
3,349,768 A 10/1967 Keane
3,362,590 A 1/1968 Gene
3,366,116 A 1/1968 Huck
3,398,848 A 8/1968 Donovan
3,400,717 A 9/1968 Bruce et al.
3,406,688 A 10/1968 Bruce
3,424,163 A 1/1969 Gravdahl
3,425,471 A 2/1969 Yates
3,434,565 A 3/1969 Fischer
3,511,241 A 5/1970 Lee
3,512,185 A 5/1970 Ellis
3,520,300 A 7/1970 Flower
3,528,423 A 9/1970 Lee
3,608,552 A 9/1971 Broerman
3,613,123 A 10/1971 Langstrom
3,648,700 A 3/1972 Warner
3,651,810 A 3/1972 Ormerod
3,661,155 A 5/1972 Lindan
3,683,918 A 8/1972 Pizzella
3,699,815 A 10/1972 Holbrook
3,721,243 A 3/1973 Greth et al.
3,726,277 A 4/1973 Hirschman
3,742,952 A 7/1973 Magers et al.
3,742,953 A 7/1973 Lee
3,757,355 A 9/1973 Allen et al.
3,788,324 A 1/1974 Lim
3,843,016 A 10/1974 Bornhorst et al.
3,863,638 A 2/1975 Rogers et al.
3,863,798 A 2/1975 Kurihara et al.
3,864,759 A 2/1975 Horiuchi
3,865,109 A 2/1975 Elmore et al.
3,881,486 A 5/1975 Fenton
3,881,489 A 5/1975 Hartwell
3,915,189 A 10/1975 Holbrook et al.
3,931,650 A 1/1976 Miller
3,964,786 A 6/1976 Mashuda
3,998,228 A 12/1976 Poidomani
3,999,550 A 12/1976 Martin
4,006,793 A 2/1977 Robinson
4,015,604 A 4/1977 Csillag
4,020,843 A 5/1977 Kanall
4,022,213 A 5/1977 Stein
4,027,776 A 6/1977 Douglas
4,031,897 A 6/1977 Graetz
4,064,962 A 12/1977 Hunt
4,069,817 A 1/1978 Fenole et al.
4,084,589 A 4/1978 Kulvi
4,096,897 A 6/1978 Cammarata
4,116,197 A 9/1978 Bermingham
4,140,739 A 2/1979 Cotten
4,180,178 A 12/1979 Turner
4,187,953 A 2/1980 Turner
4,194,508 A * 3/1980 Anderson ............... A61F 5/455 4/144.3
4,197,849 A 4/1980 Bostick
4,200,102 A 4/1980 Duhamel et al.
4,202,058 A 5/1980 Anderson
4,203,503 A 5/1980 Bertotti et al.
4,209,076 A 6/1980 Bertotti et al.
4,223,677 A 9/1980 Anderson
4,233,025 A 11/1980 Larson et al.
4,233,978 A 11/1980 Hickey
4,246,901 A 1/1981 Frosch et al.
4,253,542 A 3/1981 Ruspa et al.
4,257,418 A 3/1981 Hessner
4,270,539 A 6/1981 Frosch et al.
4,280,498 A 7/1981 Jensen
4,281,655 A 8/1981 Terauchi
4,292,916 A 10/1981 Bradley et al.
4,330,239 A 5/1982 Gannaway
4,345,341 A 8/1982 Saito
4,349,029 A 9/1982 Mott
4,352,356 A 10/1982 Tong
4,360,933 A 11/1982 Kimura et al.
4,365,363 A 12/1982 Windauer
4,375,841 A 3/1983 Vielbig
4,387,726 A 6/1983 Denard
4,403,991 A 9/1983 Hill
4,421,511 A 12/1983 Steer et al.
4,425,130 A 1/1984 Desmarais
4,446,986 A 5/1984 Bowen et al.
4,453,938 A 6/1984 Brendling
4,457,314 A 7/1984 Knowles
4,476,879 A 10/1984 Jackson
4,526,688 A 7/1985 Schmidt et al.
4,528,703 A 7/1985 Kraus
4,533,354 A 8/1985 Jensen
4,533,357 A * 8/1985 Hall ...................... A61F 13/472 604/401
D280,438 S 9/1985 Wendt
4,551,141 A 11/1985 Mcneil
4,553,968 A 11/1985 Komis
4,568,341 A 2/1986 Mitchell et al.
4,581,026 A 4/1986 Schneider
4,583,983 A 4/1986 Einhorn et al.
4,589,516 A 5/1986 Inoue et al.
4,601,716 A 7/1986 Smith
4,610,675 A 9/1986 Triunfol
4,620,333 A 11/1986 Ritter
4,626,250 A 12/1986 Schneider
4,627,846 A 12/1986 Ternstroem
4,631,061 A 12/1986 Martin
4,650,477 A 3/1987 Johnson
4,655,754 A 4/1987 Richmond et al.
4,656,675 A 4/1987 Fajnsztajn
4,681,570 A 7/1987 Dalton
4,681,572 A 7/1987 Tokarz et al.
4,681,577 A 7/1987 Stern et al.
4,692,160 A 9/1987 Nussbaumer
4,707,864 A 11/1987 Ikematsu et al.
4,713,065 A 12/1987 Koot
4,713,066 A 12/1987 Komis
4,723,953 A 2/1988 Pratt et al.

(56) References Cited

U.S. PATENT DOCUMENTS

| | | | |
|---|---|---|---|
| 4,735,841 | A | 4/1988 | Sourdet |
| 4,743,236 | A | 5/1988 | Manschot |
| 4,747,166 | A | 5/1988 | Kuntz |
| 4,752,944 | A | 6/1988 | Conrads et al. |
| 4,759,753 | A | 7/1988 | Schneider et al. |
| 4,769,215 | A | 9/1988 | Ehrenkranz |
| 4,771,484 | A | 9/1988 | Mozell |
| 4,772,280 | A | 9/1988 | Rooyakkers |
| 4,775,458 | A | 10/1988 | Forester |
| 4,784,654 | A | 11/1988 | Beecher |
| 4,790,830 | A | 12/1988 | Hamacher |
| 4,790,835 | A | 12/1988 | Elias |
| 4,791,686 | A | 12/1988 | Taniguchi et al. |
| 4,795,449 | A | 1/1989 | Schneider et al. |
| 4,798,603 | A | 1/1989 | Meyer et al. |
| 4,799,928 | A | 1/1989 | Crowley |
| 4,804,377 | A | 2/1989 | Hanifl et al. |
| 4,812,053 | A | 3/1989 | Bhattacharjee |
| 4,813,943 | A | 3/1989 | Smith |
| 4,820,291 | A | 4/1989 | Terauchi et al. |
| 4,820,297 | A | 4/1989 | Kaufman et al. |
| 4,841,728 | A | 6/1989 | Jean et al. |
| 4,846,818 | A | 7/1989 | Keldahl et al. |
| 4,846,819 | A | 7/1989 | Welch |
| 4,846,824 | A | 7/1989 | Lassen et al. |
| 4,846,909 | A | 7/1989 | Klug et al. |
| 4,865,595 | A | 9/1989 | Heyden |
| 4,880,417 | A | 11/1989 | Yabrov et al. |
| 4,882,794 | A | 11/1989 | Stewart |
| 4,883,465 | A | 11/1989 | Brennan |
| 4,886,498 | A | 12/1989 | Newton |
| 4,886,508 | A | 12/1989 | Washington |
| 4,886,509 | A | 12/1989 | Mattsson |
| 4,889,532 | A | 12/1989 | Metz et al. |
| 4,889,533 | A | 12/1989 | Beecher |
| 4,890,691 | A | 1/1990 | Ching-Ho |
| 4,895,140 | A | 1/1990 | Bellak |
| 4,903,254 | A | 2/1990 | Haas |
| 4,904,248 | A | 2/1990 | Vaillancourt |
| 4,905,692 | A | 3/1990 | More |
| 4,911,262 | A | 3/1990 | Tani et al. |
| 4,930,997 | A | 6/1990 | Bennett |
| 4,936,838 | A | 6/1990 | Cross et al. |
| 4,950,262 | A | 8/1990 | Takagi |
| 4,955,922 | A | 9/1990 | Terauchi |
| 4,957,487 | A | 9/1990 | Gerow |
| 4,965,460 | A | 10/1990 | Tanaka et al. |
| 4,986,823 | A | 1/1991 | Anderson et al. |
| 4,987,849 | A | 1/1991 | Sherman |
| 5,002,541 | A | 3/1991 | Conkling et al. |
| 5,004,463 | A | 4/1991 | Nigay |
| 5,013,308 | A | 5/1991 | Sullivan et al. |
| 5,031,248 | A | 7/1991 | Kemper |
| 5,045,077 | A | 9/1991 | Blake |
| 5,045,283 | A | 9/1991 | Patel |
| 5,049,144 | A | 9/1991 | Payton |
| 5,053,339 | A | 10/1991 | Patel |
| 5,057,092 | A | 10/1991 | Webster |
| 5,058,088 | A | 10/1991 | Haas et al. |
| 5,071,347 | A | 12/1991 | Mcguire |
| 5,078,707 | A | 1/1992 | Peter |
| 5,084,037 | A | 1/1992 | Barnett |
| 5,100,396 | A | 3/1992 | Zamierowski |
| 5,102,404 | A | 4/1992 | Goldberg et al. |
| 5,112,324 | A | 5/1992 | Wallace |
| 5,134,994 | A | 8/1992 | Say |
| 5,137,033 | A | 8/1992 | Norton |
| 5,147,301 | A | 9/1992 | Ruvio |
| 5,176,667 | A | 1/1993 | Debring |
| 5,195,997 | A | 3/1993 | Carns |
| 5,196,654 | A | 3/1993 | Diflora et al. |
| 5,199,444 | A | 4/1993 | Wheeler |
| 5,203,699 | A | 4/1993 | Mcguire |
| 5,244,458 | A | 9/1993 | Takasu |
| 5,246,454 | A | 9/1993 | Peterson |
| 5,267,988 | A | 12/1993 | Farkas |
| 5,275,307 | A | 1/1994 | Freese |
| 5,282,795 | A | 2/1994 | Finney |
| 5,294,983 | A | 3/1994 | Ersoz et al. |
| 5,295,979 | A | 3/1994 | DeLaurentis et al. |
| 5,295,983 | A | 3/1994 | Kubo |
| 5,300,052 | A | 4/1994 | Kubo |
| 5,304,749 | A | 4/1994 | Crandell |
| 5,312,383 | A | 5/1994 | Kubalak |
| 5,318,550 | A | 6/1994 | Cermak et al. |
| 5,330,457 | A | 7/1994 | Cohen |
| 5,330,459 | A | 7/1994 | Lavon et al. |
| 5,334,174 | A | 8/1994 | Street |
| 5,334,176 | A | 8/1994 | Buenger et al. |
| 5,340,840 | A | 8/1994 | Park et al. |
| 5,382,244 | A | 1/1995 | Telang |
| 5,397,315 | A | 3/1995 | Schmidt et al. |
| 5,409,014 | A | 4/1995 | Napoli et al. |
| 5,409,475 | A | 4/1995 | Steer |
| 5,411,495 | A | 5/1995 | Willingham |
| 5,423,784 | A | 6/1995 | Metz |
| 5,423,788 | A | 6/1995 | Rollins et al. |
| 5,437,836 | A | 8/1995 | Yamada |
| 5,456,246 | A | 10/1995 | Schmieding et al. |
| 5,466,229 | A | 11/1995 | Elson et al. |
| 5,478,334 | A | 12/1995 | Bernstein |
| 5,499,977 | A | 3/1996 | Marx |
| 5,543,042 | A | 8/1996 | Filan et al. |
| D373,928 | S | 9/1996 | Green |
| 5,582,604 | A | 12/1996 | Ahr et al. |
| 5,592,950 | A | 1/1997 | Kopelowicz |
| 5,593,389 | A | 1/1997 | Chang |
| 5,605,161 | A | 2/1997 | Cross |
| 5,614,699 | A | 3/1997 | Yashiro et al. |
| 5,618,277 | A | 4/1997 | Goulter |
| 5,628,735 | A | 5/1997 | Skow |
| 5,632,736 | A | 5/1997 | Block |
| 5,636,643 | A | 6/1997 | Argenta et al. |
| 5,637,104 | A | 6/1997 | Ball et al. |
| 5,662,633 | A | 9/1997 | Doak et al. |
| 5,674,212 | A | 10/1997 | Osborn et al. |
| 5,678,564 | A | 10/1997 | Lawrence et al. |
| 5,678,654 | A | 10/1997 | Uzawa |
| 5,681,297 | A | 10/1997 | Hashimoto et al. |
| 5,687,429 | A | 11/1997 | Rahlff |
| 5,695,485 | A | 12/1997 | Duperret et al. |
| 5,700,254 | A | 12/1997 | Mcdowall et al. |
| 5,701,612 | A | 12/1997 | Daneshvar |
| 5,705,777 | A | 1/1998 | Flanigan et al. |
| 5,735,835 | A | 4/1998 | Holland |
| 5,735,837 | A | 4/1998 | Ishikawa |
| 5,752,944 | A | 5/1998 | Dann et al. |
| 5,763,333 | A | 6/1998 | Suzuki et al. |
| 5,772,644 | A | 6/1998 | Bark et al. |
| 5,792,132 | A | 8/1998 | Garcia |
| 5,827,243 | A | 10/1998 | Palestrant |
| 5,827,247 | A | 10/1998 | Kay |
| 5,827,250 | A | 10/1998 | Fujioka et al. |
| 5,827,257 | A | 10/1998 | Fujioka et al. |
| D401,699 | S | 11/1998 | Herchenbach et al. |
| 5,859,393 | A | 1/1999 | Cummins et al. |
| 5,865,378 | A | 2/1999 | Hollinshead et al. |
| 5,873,869 | A | 2/1999 | Hammons et al. |
| 5,876,393 | A | 3/1999 | Ahr et al. |
| 5,887,291 | A | 3/1999 | Bellizzi |
| 5,891,125 | A | 4/1999 | Plumley |
| 5,894,608 | A | 4/1999 | Birbara |
| 5,895,349 | A | 4/1999 | Tihon |
| D409,303 | S | 5/1999 | Oepping |
| 5,911,222 | A | 6/1999 | Lawrence et al. |
| 5,956,782 | A | 9/1999 | Olguin |
| 5,957,904 | A | 9/1999 | Holland |
| 5,968,026 | A | 10/1999 | Osborn et al. |
| 5,972,505 | A | 10/1999 | Phillips et al. |
| 6,007,526 | A | 12/1999 | Passalaqua et al. |
| 6,039,060 | A | 3/2000 | Rower |
| 6,050,983 | A | 4/2000 | Moore et al. |
| 6,059,762 | A | 5/2000 | Boyer et al. |
| 6,063,064 | A | 5/2000 | Tuckey et al. |

(56) References Cited

U.S. PATENT DOCUMENTS

| | | | |
|---|---|---|---|
| 6,098,625 | A | 8/2000 | Winkler |
| 6,105,174 | A | 8/2000 | Karlsten et al. |
| 6,113,582 | A | 9/2000 | Dwork |
| 6,117,163 | A | 9/2000 | Bierman |
| 6,123,398 | A | 9/2000 | Arai et al. |
| 6,129,718 | A | 10/2000 | Wada et al. |
| 6,131,964 | A | 10/2000 | Sareshwala |
| 6,152,902 | A | 11/2000 | Christian et al. |
| 6,164,569 | A | 12/2000 | Hollinshead et al. |
| 6,177,606 | B1 | 1/2001 | Etheredge et al. |
| 6,209,142 | B1 | 4/2001 | Mattsson et al. |
| 6,220,050 | B1 | 4/2001 | Cooksey |
| 6,244,311 | B1 | 6/2001 | Hand et al. |
| 6,248,096 | B1 | 6/2001 | Dwork et al. |
| 6,263,887 | B1 | 7/2001 | Dunn |
| 6,283,246 | B1 | 9/2001 | Nishikawa |
| 6,296,627 | B1 | 10/2001 | Edwards |
| 6,311,339 | B1 | 11/2001 | Kraus |
| 6,316,688 | B1 | 11/2001 | Hammons et al. |
| 6,336,919 | B1 | 1/2002 | Davis et al. |
| 6,338,729 | B1 | 1/2002 | Wada et al. |
| 6,352,525 | B1 | 3/2002 | Wakabayashi |
| 6,394,988 | B1 | 5/2002 | Hashimoto |
| 6,395,956 | B1 | 5/2002 | Glasgow et al. |
| 6,398,742 | B1 | 6/2002 | Kim |
| 6,406,463 | B1 | 6/2002 | Brown |
| 6,409,712 | B1 | 6/2002 | Dutari et al. |
| 6,415,888 | B2 | 7/2002 | An et al. |
| 6,416,500 | B1 | 7/2002 | Wada et al. |
| 6,423,045 | B1 | 7/2002 | Wise et al. |
| 6,428,521 | B1 | 8/2002 | Droll |
| 6,428,522 | B1 | 8/2002 | Dipalma et al. |
| 6,446,454 | B1 | 9/2002 | Lee et al. |
| 6,461,340 | B1 | 10/2002 | Lenker et al. |
| 6,467,570 | B1 | 10/2002 | Herold |
| 6,475,198 | B1 | 11/2002 | Lipman et al. |
| 6,479,726 | B1 | 11/2002 | Cole et al. |
| 6,491,673 | B1 | 12/2002 | Palumbo et al. |
| 6,508,794 | B1 | 1/2003 | Palumbo et al. |
| 6,524,292 | B1 | 2/2003 | Dipalma et al. |
| 6,526,603 | B1 | 3/2003 | Murphy |
| 6,540,729 | B1 | 4/2003 | Wada et al. |
| 6,547,771 | B2 | 4/2003 | Robertson et al. |
| 6,551,293 | B1 | 4/2003 | Mitchell |
| 6,569,133 | B2 | 5/2003 | Cheng et al. |
| D476,518 | S | 7/2003 | Doppelt |
| 6,592,560 | B2 | 7/2003 | Snyder et al. |
| 6,610,038 | B1 | 8/2003 | Dipalma et al. |
| 6,618,868 | B2 | 9/2003 | Minnick |
| 6,620,142 | B1 | 9/2003 | Flueckiger |
| 6,629,651 | B1 | 10/2003 | Male et al. |
| 6,635,037 | B1 | 10/2003 | Bennett |
| 6,635,038 | B2 | 10/2003 | Scovel |
| 6,652,495 | B1 | 11/2003 | Walker |
| 6,666,850 | B1 | 12/2003 | Ahr et al. |
| 6,685,684 | B1 | 2/2004 | Falconer |
| 6,695,828 | B1 | 2/2004 | Dipalma et al. |
| 6,699,174 | B1 | 3/2004 | Bennett |
| 6,700,034 | B1 | 3/2004 | Lindsay et al. |
| 6,702,793 | B1 | 3/2004 | Sweetser et al. |
| 6,706,027 | B2 | 3/2004 | Harvie et al. |
| 6,732,384 | B2 | 5/2004 | Scott |
| 6,736,977 | B1 | 5/2004 | Hall et al. |
| 6,740,066 | B2 | 5/2004 | Wolff et al. |
| 6,764,477 | B1 | 7/2004 | Chen et al. |
| 6,783,519 | B2 | 8/2004 | Samuelsson |
| 6,796,974 | B2 | 9/2004 | Palumbo et al. |
| 6,814,547 | B2 | 11/2004 | Childers et al. |
| 6,848,719 | B2 | 2/2005 | Rowley |
| 6,849,065 | B2 | 2/2005 | Schmidt et al. |
| 6,857,137 | B2 | 2/2005 | Otto |
| 6,885,690 | B2 | 4/2005 | Aggerstam et al. |
| 6,888,044 | B2 | 5/2005 | Fell et al. |
| 6,893,425 | B2 | 5/2005 | Dunn et al. |
| 6,912,737 | B2 | 7/2005 | Ernest et al. |
| 6,918,899 | B2 | 7/2005 | Harvie |
| 6,979,324 | B2 | 12/2005 | Bybordi et al. |
| 7,018,366 | B2 | 3/2006 | Easter |
| 7,066,411 | B2 | 6/2006 | Male et al. |
| 7,087,043 | B2 | 8/2006 | Dolan |
| 7,122,023 | B1 | 10/2006 | Hinoki |
| 7,125,399 | B2 | 10/2006 | Miskie |
| 7,131,964 | B2 | 11/2006 | Harvie |
| 7,135,012 | B2 | 11/2006 | Harvie |
| 7,141,043 | B2 | 11/2006 | Harvie |
| D533,972 | S | 12/2006 | La |
| 7,160,273 | B2 | 1/2007 | Greter et al. |
| 7,166,092 | B2 | 1/2007 | Elson et al. |
| 7,171,699 | B2 | 2/2007 | Ernest et al. |
| 7,171,871 | B2 | 2/2007 | Kozak |
| 7,179,951 | B2 | 2/2007 | Krishnaswamy-Mirle et al. |
| 7,181,781 | B1 | 2/2007 | Trabold et al. |
| 7,186,245 | B1 | 3/2007 | Cheng et al. |
| 7,192,424 | B2 | 3/2007 | Cooper |
| 7,219,764 | B1 | 5/2007 | Forbes |
| 7,220,250 | B2 | 5/2007 | Suzuki et al. |
| D562,975 | S | 2/2008 | Otto |
| 7,335,189 | B2 | 2/2008 | Harvie |
| 7,358,282 | B2 | 4/2008 | Krueger et al. |
| 7,390,320 | B2 | 6/2008 | Machida et al. |
| 7,438,706 | B2 | 10/2008 | Koizumi et al. |
| 7,488,310 | B2 | 2/2009 | Yang |
| 7,491,194 | B1 | 2/2009 | Oliwa |
| D591,106 | S | 4/2009 | Dominique et al. |
| 7,513,381 | B2 | 4/2009 | Heng et al. |
| 7,520,872 | B2 | 4/2009 | Biggie et al. |
| D593,801 | S | 6/2009 | Wilson et al. |
| 7,540,364 | B2 | 6/2009 | Sanderson |
| 7,549,511 | B2 | 6/2009 | Marocco |
| 7,549,512 | B2 | 6/2009 | Newberry |
| 7,585,293 | B2 | 9/2009 | Vermaak |
| 7,588,560 | B1 | 9/2009 | Dunlop |
| 7,637,905 | B2 | 12/2009 | Saadat et al. |
| 7,658,730 | B2 | 2/2010 | Conley |
| 7,665,359 | B2 | 2/2010 | Barber |
| 7,682,347 | B2 | 3/2010 | Parks et al. |
| 7,687,004 | B2 | 3/2010 | Allen |
| 7,695,459 | B2 | 4/2010 | Gilbert et al. |
| 7,695,460 | B2 | 4/2010 | Wada et al. |
| 7,699,818 | B2 | 4/2010 | Gilbert |
| 7,699,831 | B2 | 4/2010 | Bengtson et al. |
| 7,722,584 | B2 | 5/2010 | Tanaka et al. |
| 7,727,206 | B2 | 6/2010 | Gorres |
| 7,740,620 | B2 | 6/2010 | Gilbert et al. |
| 7,749,205 | B2 | 7/2010 | Tazoe et al. |
| 7,755,497 | B2 | 7/2010 | Wada et al. |
| 7,766,887 | B2 | 8/2010 | Burns et al. |
| 7,803,144 | B1 | 9/2010 | Vollrath |
| D625,407 | S | 10/2010 | Koizumi et al. |
| 7,806,879 | B2 | 10/2010 | Brooks et al. |
| 7,811,272 | B2 | 10/2010 | Lindsay et al. |
| 7,815,067 | B2 | 10/2010 | Matsumoto et al. |
| 7,833,169 | B2 | 11/2010 | Hannon |
| 7,857,806 | B2 | 12/2010 | Karpowicz et al. |
| 7,866,942 | B2 | 1/2011 | Harvie |
| 7,871,385 | B2 | 1/2011 | Levinson et al. |
| 7,875,010 | B2 | 1/2011 | Frazier et al. |
| 7,901,389 | B2 | 3/2011 | Mombrinie |
| 7,927,320 | B2 | 4/2011 | Goldwasser et al. |
| 7,927,321 | B2 | 4/2011 | Marland |
| 7,931,634 | B2 | 4/2011 | Swiecicki et al. |
| 7,939,706 | B2 | 5/2011 | Okabe et al. |
| 7,946,443 | B2 | 5/2011 | Stull et al. |
| 7,947,025 | B2 | 5/2011 | Buglino et al. |
| 7,963,419 | B2 | 6/2011 | Burney et al. |
| 7,976,519 | B2 | 7/2011 | Bubb et al. |
| 7,993,318 | B2 | 8/2011 | Olsson et al. |
| 8,015,627 | B2 | 9/2011 | Baker et al. |
| 8,016,071 | B1 | 9/2011 | Martinus et al. |
| 8,028,460 | B2 | 10/2011 | Williams |
| 8,047,398 | B2 | 11/2011 | Dimartino et al. |
| 8,083,094 | B2 | 12/2011 | Caulfield et al. |
| 8,128,608 | B2 | 3/2012 | Thevenin |
| 8,167,860 | B1 | 5/2012 | Siegel |

(56) References Cited

U.S. PATENT DOCUMENTS

| | | | |
|---|---|---|---|
| 8,181,651 | B2 | 5/2012 | Pinel |
| 8,181,819 | B2 | 5/2012 | Burney et al. |
| 8,211,063 | B2 | 7/2012 | Bierman et al. |
| 8,221,369 | B2 | 7/2012 | Parks et al. |
| 8,241,262 | B2 | 8/2012 | Mahnensmith |
| 8,277,426 | B2 | 10/2012 | Wilcox et al. |
| 8,287,508 | B1 | 10/2012 | Sanchez |
| 8,303,554 | B2 | 11/2012 | Tsai et al. |
| 8,322,565 | B2 | 12/2012 | Caulfield et al. |
| 8,337,477 | B2 | 12/2012 | Parks et al. |
| D674,241 | S | 1/2013 | Bickert et al. |
| 8,343,122 | B2 | 1/2013 | Gorres |
| 8,343,125 | B2 | 1/2013 | Kawazoe et al. |
| 8,353,074 | B2 | 1/2013 | Krebs |
| 8,353,886 | B2 | 1/2013 | Bester et al. |
| D676,241 | S | 2/2013 | Merrill |
| 8,388,587 | B1 | 3/2013 | Gmuer et al. |
| 8,388,588 | B2 | 3/2013 | Wada et al. |
| D679,807 | S | 4/2013 | Burgess et al. |
| 8,425,482 | B2 | 4/2013 | Khoubnazar |
| 8,434,586 | B2 | 5/2013 | Pawelski et al. |
| 8,449,510 | B2 | 5/2013 | Martini et al. |
| D684,260 | S | 6/2013 | Lund et al. |
| 8,470,230 | B2 | 6/2013 | Caulfield et al. |
| 8,479,941 | B2 | 7/2013 | Matsumoto et al. |
| 8,479,949 | B2 | 7/2013 | Henkel |
| 8,500,719 | B1 | 8/2013 | Simpson et al. |
| 8,512,301 | B2 | 8/2013 | Ma |
| 8,529,530 | B2 | 9/2013 | Koch et al. |
| 8,535,284 | B2 | 9/2013 | Joder et al. |
| 8,546,639 | B2 | 10/2013 | Wada et al. |
| 8,551,062 | B2 | 10/2013 | Kay |
| 8,551,075 | B2 | 10/2013 | Bengtson |
| 8,568,376 | B2 | 10/2013 | Delattre et al. |
| D694,404 | S | 11/2013 | Burgess et al. |
| 8,585,683 | B2 | 11/2013 | Bengtson et al. |
| 8,586,583 | B2 | 11/2013 | Hamblin et al. |
| 8,652,112 | B2 | 2/2014 | Johannison et al. |
| 8,669,412 | B2 | 3/2014 | Fernkvist et al. |
| D702,973 | S | 4/2014 | Norland et al. |
| 8,703,032 | B2 | 4/2014 | Menon et al. |
| D704,330 | S | 5/2014 | Cicatelli |
| D704,510 | S | 5/2014 | Mason et al. |
| D705,423 | S | 5/2014 | Walsh Cutler |
| D705,926 | S | 5/2014 | Burgess et al. |
| 8,714,394 | B2 | 5/2014 | Wulf |
| 8,715,267 | B2 | 5/2014 | Bengtson et al. |
| 8,757,425 | B2 | 6/2014 | Copeland |
| 8,777,032 | B2 | 7/2014 | Biesecker et al. |
| 8,808,260 | B2 | 8/2014 | Koch et al. |
| 8,864,730 | B2 | 10/2014 | Conway et al. |
| 8,881,923 | B2 | 11/2014 | Higginson |
| 8,882,731 | B2 | 11/2014 | Suzuki et al. |
| 8,936,585 | B2 | 1/2015 | Carson et al. |
| D729,581 | S | 5/2015 | Boroski |
| 9,028,460 | B2 | 5/2015 | Medeiros |
| 9,056,698 | B2 | 6/2015 | Noer |
| 9,078,792 | B2 | 7/2015 | Ruiz |
| 9,145,879 | B2 | 9/2015 | Pirovano et al. |
| 9,173,602 | B2 | 11/2015 | Gilbert |
| 9,173,799 | B2 | 11/2015 | Tanimoto et al. |
| 9,187,220 | B2 | 11/2015 | Biesecker et al. |
| 9,199,772 | B2 | 12/2015 | Krippendorf |
| 9,233,020 | B2 | 1/2016 | Matsumiya |
| 9,248,058 | B2 | 2/2016 | Conway et al. |
| 9,308,118 | B1 | 4/2016 | Dupree et al. |
| 9,309,029 | B2 | 4/2016 | Incorvia et al. |
| 9,333,281 | B2 | 5/2016 | Giezendanner et al. |
| 9,381,108 | B2 | 7/2016 | Longoni et al. |
| 9,382,047 | B2 | 7/2016 | Schmidtner et al. |
| 9,402,424 | B2 | 8/2016 | Roy |
| 9,456,937 | B2 | 10/2016 | Ellis |
| 9,480,595 | B2 | 11/2016 | Baham et al. |
| 9,517,865 | B2 | 12/2016 | Albers et al. |
| D777,941 | S | 1/2017 | Piramoon |
| 9,533,806 | B2 | 1/2017 | Ding et al. |
| 9,550,611 | B2 | 1/2017 | Hodge |
| 9,555,930 | B2 | 1/2017 | Campbell et al. |
| 9,623,159 | B2 | 4/2017 | Locke |
| D789,522 | S | 6/2017 | Burgess et al. |
| 9,687,849 | B2 | 6/2017 | Bruno et al. |
| 9,694,949 | B2 | 7/2017 | Hendricks et al. |
| 9,709,048 | B2 | 7/2017 | Kinjo |
| 9,713,547 | B2 | 7/2017 | Lee et al. |
| 9,732,754 | B2 | 8/2017 | Huang et al. |
| 9,737,433 | B2 | 8/2017 | Joh |
| 9,752,564 | B2 | 9/2017 | Arceno et al. |
| 9,788,992 | B2 | 10/2017 | Harvie |
| D804,907 | S | 12/2017 | Sandoval |
| 9,868,564 | B2 | 1/2018 | Mcgirr et al. |
| D814,239 | S | 4/2018 | Arora |
| D817,484 | S | 5/2018 | Lafond |
| 9,968,908 | B2 | 5/2018 | Ladrech et al. |
| 10,010,393 | B1 | 7/2018 | Nguyen et al. |
| 10,037,640 | B2 | 7/2018 | Gordon |
| 10,058,470 | B2 | 8/2018 | Phillips |
| 10,098,990 | B2 | 10/2018 | Koch et al. |
| D835,264 | S | 12/2018 | Mozzicato et al. |
| D835,779 | S | 12/2018 | Mozzicato et al. |
| D840,533 | S | 2/2019 | Mozzicato et al. |
| D840,534 | S | 2/2019 | Mozzicato et al. |
| 10,225,376 | B2 | 3/2019 | Perez Martinez |
| 10,226,376 | B2 | 3/2019 | Sanchez et al. |
| 10,258,517 | B1 | 4/2019 | Maschino et al. |
| D848,612 | S | 5/2019 | Mozzicato et al. |
| 10,307,305 | B1 | 6/2019 | Hodges |
| 10,335,121 | B2 | 7/2019 | Desai |
| D856,512 | S | 8/2019 | Cowart et al. |
| 10,376,406 | B2 | 8/2019 | Newton |
| 10,376,407 | B2 | 8/2019 | Newton |
| 10,390,989 | B2 | 8/2019 | Sanchez et al. |
| D858,144 | S | 9/2019 | Fu |
| 10,406,039 | B2 | 9/2019 | Villarreal |
| 10,407,222 | B2 | 9/2019 | Allen |
| 10,478,356 | B2 | 11/2019 | Griffin |
| 10,500,108 | B1 | 12/2019 | Maschino et al. |
| 10,502,198 | B2 | 12/2019 | Stumpf et al. |
| 10,538,366 | B2 | 1/2020 | Pentelovitch et al. |
| 10,569,938 | B2 | 2/2020 | Zhao et al. |
| 10,577,156 | B2 | 3/2020 | Dagnelie et al. |
| RE47,930 | E | 4/2020 | Cho |
| 10,618,721 | B2 | 4/2020 | Vazin |
| D884,390 | S | 5/2020 | Wang |
| 10,669,079 | B2 | 6/2020 | Freedman et al. |
| D892,315 | S | 8/2020 | Airy |
| 10,730,672 | B2 | 8/2020 | Bertram et al. |
| 10,737,848 | B2 | 8/2020 | Philip et al. |
| 10,765,854 | B2 | 9/2020 | Law et al. |
| 10,766,670 | B2 | 9/2020 | Kittmann |
| 10,799,386 | B1 | 10/2020 | Harrison |
| 10,806,623 | B2 | 10/2020 | VanMiddendorp et al. |
| 10,806,642 | B2 | 10/2020 | Tagomori et al. |
| D901,214 | S | 11/2020 | Hu |
| 10,849,799 | B2 | 12/2020 | Nishikawa et al. |
| 10,857,025 | B2 | 12/2020 | Davis et al. |
| 10,865,017 | B1 | 12/2020 | Cowart et al. |
| 10,889,412 | B2 | 1/2021 | West et al. |
| 10,913,581 | B2 | 2/2021 | Stahlecker |
| D912,244 | S | 3/2021 | Rehm et al. |
| 10,952,889 | B2 | 3/2021 | Newton et al. |
| 10,973,378 | B2 | 4/2021 | Ryu et al. |
| 10,973,678 | B2 | 4/2021 | Newton et al. |
| 10,974,874 | B2 | 4/2021 | Ragias et al. |
| 11,000,401 | B2 | 5/2021 | Ecklund et al. |
| 11,002,165 | B2 | 5/2021 | Poulin |
| D923,365 | S | 6/2021 | Wang |
| 11,026,829 | B2 | 6/2021 | Harvie |
| 11,027,900 | B2 | 6/2021 | Liu |
| 11,045,346 | B2 | 6/2021 | Argent et al. |
| D928,946 | S | 8/2021 | Sanchez et al. |
| 11,090,183 | B2 | 8/2021 | Sanchez et al. |
| 11,160,695 | B2 | 11/2021 | Febo et al. |
| 11,160,697 | B2 | 11/2021 | Maschino et al. |
| 11,168,420 | B2 | 11/2021 | Kinugasa et al. |

(56) References Cited

U.S. PATENT DOCUMENTS

| | | | |
|---|---|---|---|
| 11,179,506 | B2 | 11/2021 | Barr et al. |
| 11,199,116 | B2 | 12/2021 | Ostromecki et al. |
| 11,207,206 | B2 | 12/2021 | Sharma et al. |
| 11,226,376 | B2 | 1/2022 | Yamauchi et al. |
| 11,253,389 | B2 | 2/2022 | Sharma et al. |
| 11,253,407 | B2 | 2/2022 | Miao et al. |
| 11,326,586 | B2 | 5/2022 | Milner et al. |
| 11,369,508 | B2 | 6/2022 | Ecklund et al. |
| 11,369,524 | B2 | 6/2022 | Hubbard et al. |
| 11,376,152 | B2 | 7/2022 | Sanchez et al. |
| 11,382,786 | B2 | 7/2022 | Sanchez et al. |
| 11,382,788 | B2 | 7/2022 | Hjorth et al. |
| 11,389,318 | B2 | 7/2022 | Radl et al. |
| 11,395,871 | B2 | 7/2022 | Radl et al. |
| 11,399,990 | B2 | 8/2022 | Suyama |
| 11,426,303 | B2 | 8/2022 | Davis et al. |
| 11,504,265 | B2 | 11/2022 | Godinez et al. |
| 11,529,252 | B2 | 12/2022 | Glithero et al. |
| 11,547,788 | B2 | 1/2023 | Radl et al. |
| 11,806,266 | B2 | 11/2023 | Sanchez et al. |
| 11,839,567 | B2 | 12/2023 | Davis et al. |
| D1,010,109 | S | 1/2024 | Ecklund et al. |
| 11,857,716 | B2 | 1/2024 | Lee et al. |
| 11,865,030 | B2 | 1/2024 | Davis et al. |
| 11,890,221 | B2 | 2/2024 | Ulreich et al. |
| 11,911,160 | B2 | 2/2024 | Woodard et al. |
| 11,925,575 | B2 | 3/2024 | Newton |
| 11,938,053 | B2 | 3/2024 | Austermann et al. |
| 11,944,740 | B2 | 4/2024 | Hughett et al. |
| 11,994,122 | B2 | 5/2024 | Bodain |
| 11,998,475 | B2 | 6/2024 | Becker et al. |
| 12,023,457 | B2 | 7/2024 | Mann et al. |
| 12,042,422 | B2 | 7/2024 | Davis et al. |
| D1,038,385 | S | 8/2024 | Ecklund et al. |
| 12,064,372 | B2 | 8/2024 | Godinez et al. |
| 12,070,432 | B2 | 8/2024 | Tourchak et al. |
| 12,090,083 | B2 | 9/2024 | Ecklund et al. |
| 12,121,468 | B2 | 10/2024 | Sanchez et al. |
| 12,133,813 | B2 | 11/2024 | Ulreich et al. |
| 12,138,195 | B2 | 11/2024 | Alder et al. |
| 12,186,229 | B2 | 1/2025 | Davis et al. |
| 12,193,962 | B2 | 1/2025 | Newton et al. |
| 12,245,966 | B2 | 3/2025 | Newton |
| 12,274,638 | B2 | 4/2025 | Spector |
| 2001/0037097 | A1 | 11/2001 | Cheng et al. |
| 2001/0037098 | A1 | 11/2001 | Snyder |
| 2001/0054426 | A1 | 12/2001 | Knudson et al. |
| 2002/0019614 | A1 | 2/2002 | Woon |
| 2002/0026161 | A1 | 2/2002 | Grundke |
| 2002/0026163 | A1 | 2/2002 | Grundke |
| 2002/0042945 | A1 | 4/2002 | Sands |
| 2002/0087131 | A1 | 7/2002 | Wolff et al. |
| 2002/0091364 | A1 | 7/2002 | Prabhakar |
| 2002/0189992 | A1 | 12/2002 | Schmidt et al. |
| 2002/0193760 | A1 | 12/2002 | Thompson |
| 2002/0193762 | A1 | 12/2002 | Suydam |
| 2003/0004436 | A1 | 1/2003 | Schmidt et al. |
| 2003/0032931 | A1 | 2/2003 | Grundke et al. |
| 2003/0032944 | A1 | 2/2003 | Cawood |
| 2003/0073964 | A1 | 4/2003 | Palumbo et al. |
| 2003/0074724 | A1 | 4/2003 | Sands |
| 2003/0120178 | A1 | 6/2003 | Heki |
| 2003/0129178 | A1 | 7/2003 | Wegman et al. |
| 2003/0157859 | A1 | 8/2003 | Ishikawa |
| 2003/0181880 | A1 | 9/2003 | Schwartz |
| 2003/0195484 | A1 | 10/2003 | Harvie |
| 2003/0204173 | A1 | 10/2003 | Burns et al. |
| 2003/0233079 | A1 | 12/2003 | Parks et al. |
| 2004/0006321 | A1 | 1/2004 | Cheng et al. |
| 2004/0015141 | A1 | 1/2004 | Cheng et al. |
| 2004/0056122 | A1 | 3/2004 | Male et al. |
| 2004/0084465 | A1 | 5/2004 | Luburic |
| 2004/0127872 | A1 | 7/2004 | Petryk et al. |
| 2004/0128749 | A1 | 7/2004 | Scott |
| 2004/0143229 | A1 | 7/2004 | Easter |
| 2004/0147863 | A1 | 7/2004 | Diaz et al. |
| 2004/0147894 | A1 | 7/2004 | Mizutani et al. |
| 2004/0147895 | A1 | 7/2004 | Mizutani et al. |
| 2004/0158221 | A1 | 8/2004 | Mizutani et al. |
| 2004/0176731 | A1 | 9/2004 | Cheng et al. |
| 2004/0176746 | A1 | 9/2004 | Forral |
| 2004/0181201 | A1 | 9/2004 | Mizutani et al. |
| 2004/0191919 | A1 | 9/2004 | Unger et al. |
| 2004/0194792 | A1 | 10/2004 | Zhuang et al. |
| 2004/0200936 | A1 | 10/2004 | Opperthauser |
| 2004/0207530 | A1 | 10/2004 | Nielsen |
| 2004/0236292 | A1 | 11/2004 | Tazoe et al. |
| 2004/0243075 | A1 | 12/2004 | Harvie |
| 2004/0254547 | A1 | 12/2004 | Okabe et al. |
| 2005/0010182 | A1 | 1/2005 | Parks et al. |
| 2005/0010197 | A1 | 1/2005 | Lau et al. |
| 2005/0033248 | A1 | 2/2005 | Machida et al. |
| 2005/0065471 | A1 | 3/2005 | Kuntz |
| 2005/0070861 | A1 | 3/2005 | Okabe et al. |
| 2005/0070862 | A1 | 3/2005 | Tazoe et al. |
| 2005/0082300 | A1 | 4/2005 | Modrell et al. |
| 2005/0097662 | A1 | 5/2005 | Leimkuhler et al. |
| 2005/0101924 | A1 | 5/2005 | Elson et al. |
| 2005/0119630 | A1 | 6/2005 | Harvie |
| 2005/0131361 | A1 | 6/2005 | Miskie |
| 2005/0137557 | A1 | 6/2005 | Swiecicki et al. |
| 2005/0137560 | A1 | 6/2005 | Mizutani et al. |
| 2005/0137561 | A1 | 6/2005 | Mizutani et al. |
| 2005/0148984 | A1 | 7/2005 | Lindsay et al. |
| 2005/0154360 | A1 | 7/2005 | Harvie |
| 2005/0177070 | A1 | 8/2005 | Levinson et al. |
| 2005/0197639 | A1 | 9/2005 | Mombrinie |
| 2005/0197645 | A1 | 9/2005 | Karpowicz et al. |
| 2005/0215969 | A1 | 9/2005 | Mizutani et al. |
| 2005/0273069 | A1 | 12/2005 | Mizutani et al. |
| 2005/0273920 | A1 | 12/2005 | Marinas |
| 2005/0277903 | A1 | 12/2005 | Mizutani et al. |
| 2005/0277904 | A1 | 12/2005 | Chase et al. |
| 2005/0279359 | A1 | 12/2005 | Leblanc et al. |
| 2006/0004332 | A1 | 1/2006 | Marx |
| 2006/0015080 | A1 | 1/2006 | Mahnensmith |
| 2006/0015081 | A1 | 1/2006 | Suzuki et al. |
| 2006/0016778 | A1 | 1/2006 | Park |
| 2006/0069359 | A1 | 3/2006 | Dipalma et al. |
| 2006/0079854 | A1 | 4/2006 | Kay et al. |
| 2006/0111648 | A1 | 5/2006 | Vermaak |
| 2006/0113334 | A1 | 6/2006 | Mikhail et al. |
| 2006/0155214 | A1 | 7/2006 | Wightman |
| 2006/0171997 | A1 | 8/2006 | Gruenbacher et al. |
| 2006/0180566 | A1 | 8/2006 | Mataya |
| 2006/0200102 | A1 | 9/2006 | Cooper |
| 2006/0229575 | A1 | 10/2006 | Boiarski |
| 2006/0229576 | A1 | 10/2006 | Conway et al. |
| 2006/0231648 | A1 | 10/2006 | Male et al. |
| 2006/0235266 | A1 | 10/2006 | Nan |
| 2006/0235359 | A1 | 10/2006 | Marland |
| 2006/0241553 | A1 | 10/2006 | Harvie |
| 2006/0269439 | A1 | 11/2006 | White |
| 2006/0277670 | A1 | 12/2006 | Baker et al. |
| 2007/0006368 | A1 | 1/2007 | Key et al. |
| 2007/0010797 | A1 | 1/2007 | Nishtala et al. |
| 2007/0016152 | A1 | 1/2007 | Karpowicz et al. |
| 2007/0025886 | A1 | 2/2007 | Yong |
| 2007/0038194 | A1 | 2/2007 | Wada et al. |
| 2007/0055209 | A1 | 3/2007 | Patel et al. |
| 2007/0073252 | A1 | 3/2007 | Forgrave |
| 2007/0117880 | A1 | 5/2007 | Elson et al. |
| 2007/0118993 | A1 | 5/2007 | Bates |
| 2007/0135786 | A1 | 6/2007 | Schmidt et al. |
| 2007/0137718 | A1 | 6/2007 | Rushlander et al. |
| 2007/0149935 | A1 | 6/2007 | Dirico |
| 2007/0191804 | A1 | 8/2007 | Coley |
| 2007/0203464 | A1 | 8/2007 | Green et al. |
| 2007/0214553 | A1 | 9/2007 | Carromba et al. |
| 2007/0225663 | A1 | 9/2007 | Watt et al. |
| 2007/0225666 | A1 | 9/2007 | Otto |
| 2007/0225668 | A1 | 9/2007 | Otto |
| 2007/0266486 | A1 | 11/2007 | Ramirez |
| 2007/0282309 | A1 | 12/2007 | Bengtson et al. |

(56) References Cited

U.S. PATENT DOCUMENTS

| | | | |
|---|---|---|---|
| 2008/0004576 | A1 | 1/2008 | Tanaka et al. |
| 2008/0015526 | A1 | 1/2008 | Reiner et al. |
| 2008/0015527 | A1 | 1/2008 | House |
| 2008/0033386 | A1 | 2/2008 | Okabe et al. |
| 2008/0041869 | A1 | 2/2008 | Backaert |
| 2008/0077099 | A1 | 3/2008 | House |
| 2008/0091153 | A1 | 4/2008 | Harvie |
| 2008/0091158 | A1 | 4/2008 | Yang |
| 2008/0114327 | A1 | 5/2008 | Barge |
| 2008/0167634 | A1 | 7/2008 | Kouta et al. |
| 2008/0183157 | A1 | 7/2008 | Walters |
| 2008/0215031 | A1 | 9/2008 | Belfort et al. |
| 2008/0234642 | A1 | 9/2008 | Patterson et al. |
| 2008/0269703 | A1 | 10/2008 | Collins et al. |
| 2008/0281282 | A1 | 11/2008 | Finger et al. |
| 2008/0287894 | A1 | 11/2008 | Van Den Heuvel et al. |
| 2008/0312550 | A1 | 12/2008 | Nishtala et al. |
| 2009/0025717 | A1 | 1/2009 | Pinel |
| 2009/0048570 | A1 | 2/2009 | Jensen |
| 2009/0056003 | A1 | 3/2009 | Ivie et al. |
| 2009/0069761 | A1 | 3/2009 | Vogel |
| 2009/0069765 | A1 | 3/2009 | Wortham |
| 2009/0120179 | A1 | 5/2009 | Nylander et al. |
| 2009/0192482 | A1 | 7/2009 | Dodge et al. |
| 2009/0226541 | A1 | 9/2009 | Scholz et al. |
| 2009/0234312 | A1 | 9/2009 | Otoole et al. |
| 2009/0251510 | A1 | 10/2009 | Noro et al. |
| 2009/0259206 | A1 | 10/2009 | Kai et al. |
| 2009/0264840 | A1 | 10/2009 | Virginio |
| 2009/0270822 | A1 | 10/2009 | Medeiros |
| 2009/0281510 | A1 | 11/2009 | Fisher |
| 2009/0283982 | A1 | 11/2009 | Thomas |
| 2009/0306610 | A1 | 12/2009 | Van Den Heuvel et al. |
| 2010/0004612 | A1 | 1/2010 | Thevenin |
| 2010/0030189 | A1 | 2/2010 | Fleming |
| 2010/0031429 | A1 | 2/2010 | Kim et al. |
| 2010/0032789 | A1 | 2/2010 | Schoen et al. |
| 2010/0058660 | A1 | 3/2010 | Williams |
| 2010/0121289 | A1 | 5/2010 | Parks et al. |
| 2010/0158168 | A1 | 6/2010 | Murthy et al. |
| 2010/0160882 | A1 | 6/2010 | Lowe |
| 2010/0174250 | A1 | 7/2010 | Hu et al. |
| 2010/0179493 | A1 | 7/2010 | Heagle et al. |
| 2010/0185168 | A1 | 7/2010 | Graauw et al. |
| 2010/0198172 | A1 | 8/2010 | Wada et al. |
| 2010/0211032 | A1 | 8/2010 | Tsai et al. |
| 2010/0234820 | A1 | 9/2010 | Tsai et al. |
| 2010/0241104 | A1 | 9/2010 | Gilbert |
| 2010/0263113 | A1 | 10/2010 | Shelton et al. |
| 2010/0310845 | A1 | 12/2010 | Bond et al. |
| 2011/0028920 | A1 | 2/2011 | Johannison |
| 2011/0028922 | A1 | 2/2011 | Kay et al. |
| 2011/0034889 | A1 | 2/2011 | Smith |
| 2011/0036837 | A1 | 2/2011 | Shang |
| 2011/0040267 | A1 | 2/2011 | Wada et al. |
| 2011/0040271 | A1 | 2/2011 | Rogers et al. |
| 2011/0054426 | A1 | 3/2011 | Stewart et al. |
| 2011/0060299 | A1 | 3/2011 | Wada et al. |
| 2011/0060300 | A1 | 3/2011 | Weig et al. |
| 2011/0077495 | A1 | 3/2011 | Gilbert |
| 2011/0077606 | A1 | 3/2011 | Wilcox et al. |
| 2011/0087337 | A1 | 4/2011 | Forsell |
| 2011/0137273 | A1 | 6/2011 | Muellejans et al. |
| 2011/0145993 | A1 | 6/2011 | Rader et al. |
| 2011/0152802 | A1 | 6/2011 | Dicamillo et al. |
| 2011/0164147 | A1 | 7/2011 | Takahashi et al. |
| 2011/0172620 | A1 | 7/2011 | Khambatta |
| 2011/0172625 | A1 | 7/2011 | Wada et al. |
| 2011/0198904 | A1 | 8/2011 | Thomas et al. |
| 2011/0202024 | A1 | 8/2011 | Cozzens |
| 2011/0238023 | A1 | 9/2011 | Slayton |
| 2011/0240648 | A1 | 10/2011 | Tucker |
| 2011/0251572 | A1 | 10/2011 | Nishtala et al. |
| 2011/0265889 | A1 | 11/2011 | Tanaka et al. |
| 2011/0276020 | A1 | 11/2011 | Mitsui |
| 2012/0029452 | A1 | 2/2012 | Roedsten |
| 2012/0035577 | A1 | 2/2012 | Tomes et al. |
| 2012/0041400 | A1 | 2/2012 | Christensen |
| 2012/0059328 | A1 | 3/2012 | Dikeman et al. |
| 2012/0066825 | A1 | 3/2012 | Birbara et al. |
| 2012/0103347 | A1 | 5/2012 | Wheaton et al. |
| 2012/0116336 | A1 | 5/2012 | Sharma et al. |
| 2012/0137420 | A1 | 6/2012 | Gordon et al. |
| 2012/0165768 | A1 | 6/2012 | Sekiyama et al. |
| 2012/0165786 | A1 | 6/2012 | Chappa et al. |
| 2012/0209216 | A1 | 8/2012 | Jensen et al. |
| 2012/0209225 | A1 | 8/2012 | Hu et al. |
| 2012/0210503 | A1 | 8/2012 | Anzivino et al. |
| 2012/0233761 | A1 | 9/2012 | Huang |
| 2012/0245541 | A1 | 9/2012 | Suzuki et al. |
| 2012/0245542 | A1 | 9/2012 | Suzuki et al. |
| 2012/0245547 | A1 | 9/2012 | Wilcox et al. |
| 2012/0253303 | A1 | 10/2012 | Suzuki et al. |
| 2012/0271259 | A1 | 10/2012 | Ulert |
| 2012/0296305 | A1 | 11/2012 | Barraza Khaled et al. |
| 2012/0316522 | A1 | 12/2012 | Carter et al. |
| 2012/0330256 | A1 | 12/2012 | Wilcox et al. |
| 2013/0006206 | A1 | 1/2013 | Wada et al. |
| 2013/0019374 | A1 | 1/2013 | Schwartz |
| 2013/0045651 | A1 | 2/2013 | Esteves et al. |
| 2013/0053804 | A1 | 2/2013 | Soerensen et al. |
| 2013/0096523 | A1 | 4/2013 | Chang et al. |
| 2013/0110059 | A1 | 5/2013 | Kossow et al. |
| 2013/0138064 | A1 | 5/2013 | Stroebech et al. |
| 2013/0144240 | A1 | 6/2013 | Ellis |
| 2013/0150813 | A1 | 6/2013 | Gordon et al. |
| 2013/0158494 | A1 | 6/2013 | Ong et al. |
| 2013/0165880 | A1 | 6/2013 | Amos et al. |
| 2013/0218112 | A1 | 8/2013 | Thompson |
| 2013/0245496 | A1 | 9/2013 | Wells et al. |
| 2013/0245586 | A1 | 9/2013 | Jha |
| 2013/0274711 | A1 | 10/2013 | O'Day |
| 2013/0292537 | A1 | 11/2013 | Dirico |
| 2013/0330501 | A1 | 12/2013 | Aizenberg et al. |
| 2014/0005647 | A1 | 1/2014 | Shuffler et al. |
| 2014/0031774 | A1 | 1/2014 | Bengtson |
| 2014/0039432 | A1 | 2/2014 | Dunbar et al. |
| 2014/0039440 | A1 | 2/2014 | Doescher |
| 2014/0058347 | A1 | 2/2014 | Marquette |
| 2014/0107599 | A1 | 4/2014 | Fink et al. |
| 2014/0157499 | A1 | 6/2014 | Suzuki et al. |
| 2014/0171889 | A1 | 6/2014 | Hopman et al. |
| 2014/0182051 | A1 | 7/2014 | Tanimoto et al. |
| 2014/0196189 | A1 | 7/2014 | Lee et al. |
| 2014/0257231 | A1 | 9/2014 | Wang et al. |
| 2014/0276501 | A1 | 9/2014 | Cisko |
| 2014/0303582 | A1 | 10/2014 | Wright et al. |
| 2014/0316381 | A1 | 10/2014 | Reglin |
| 2014/0325746 | A1 | 11/2014 | Block |
| 2014/0348139 | A1 | 11/2014 | Gomez Martinez |
| 2014/0352050 | A1 | 12/2014 | Yao et al. |
| 2014/0371628 | A1 | 12/2014 | Desai |
| 2015/0045757 | A1 | 2/2015 | Lee et al. |
| 2015/0047114 | A1 | 2/2015 | Ramirez |
| 2015/0048089 | A1 | 2/2015 | Robertson |
| 2015/0135423 | A1 | 5/2015 | Sharpe et al. |
| 2015/0157300 | A1 | 6/2015 | Ealovega et al. |
| 2015/0209188 | A1 | 7/2015 | Scheremet et al. |
| 2015/0209194 | A1 | 7/2015 | Heyman |
| 2015/0267862 | A1 | 9/2015 | Mishler |
| 2015/0290421 | A1 | 10/2015 | Glickman et al. |
| 2015/0290425 | A1 | 10/2015 | Macy et al. |
| 2015/0320583 | A1 | 11/2015 | Harvie |
| 2015/0329255 | A1 | 11/2015 | Rzepecki |
| 2015/0342799 | A1 | 12/2015 | Michiels et al. |
| 2015/0359660 | A1 | 12/2015 | Harvie |
| 2015/0359996 | A1 | 12/2015 | Arora et al. |
| 2015/0366699 | A1 | 12/2015 | Nelson |
| 2016/0008193 | A1 | 1/2016 | Schulke |
| 2016/0029998 | A1 | 2/2016 | Brister et al. |
| 2016/0030228 | A1 | 2/2016 | Jones |
| 2016/0038356 | A1 | 2/2016 | Yao et al. |
| 2016/0051395 | A1 | 2/2016 | Ugarte M.D. |
| 2016/0058322 | A1 | 3/2016 | Brister et al. |

(56) References Cited

U.S. PATENT DOCUMENTS

2016/0060001 A1 3/2016 Wada et al.
2016/0100976 A1 4/2016 Conway et al.
2016/0106604 A1 4/2016 Timm
2016/0113809 A1 4/2016 Kim
2016/0135792 A1 5/2016 Cai
2016/0136338 A1 5/2016 Lee et al.
2016/0183689 A1 6/2016 Miner
2016/0256022 A1 9/2016 Le
2016/0270982 A1 9/2016 Raycheck et al.
2016/0278662 A1 9/2016 Brister et al.
2016/0357400 A1 12/2016 Penha et al.
2016/0366699 A1 12/2016 Zhang et al.
2016/0367226 A1 12/2016 Newton et al.
2016/0367411 A1 12/2016 Justiz et al.
2016/0367726 A1 12/2016 Gratzer
2016/0374848 A1 12/2016 Sanchez et al.
2017/0007438 A1 1/2017 Harvie
2017/0014560 A1 1/2017 Minskoff et al.
2017/0042724 A1 2/2017 Ugarte
2017/0042748 A1 2/2017 Griffin
2017/0100276 A1 4/2017 Joh
2017/0107312 A1 4/2017 Hinayama et al.
2017/0128638 A1 5/2017 Giezendanner et al.
2017/0136209 A1 5/2017 Burnett et al.
2017/0143534 A1 5/2017 Sanchez
2017/0165100 A1 6/2017 Jackson et al.
2017/0165405 A1 6/2017 Muser et al.
2017/0189225 A1 7/2017 Voorhees et al.
2017/0202692 A1 7/2017 Laniado
2017/0216081 A1 8/2017 Accosta
2017/0238911 A1 8/2017 Duval
2017/0246026 A1 8/2017 Laniado
2017/0252014 A1 9/2017 Siller Gonzalez et al.
2017/0252202 A9 9/2017 Sanchez et al.
2017/0266031 A1 9/2017 Sanchez et al.
2017/0266658 A1 9/2017 Bruno et al.
2017/0281399 A1 10/2017 Vanmiddendorp et al.
2017/0281419 A1 10/2017 Pintado
2017/0312116 A1 11/2017 Laniado
2017/0325788 A1 11/2017 Ealovega et al.
2017/0333244 A1 11/2017 Laniado
2017/0348139 A1 12/2017 Newton et al.
2017/0354532 A1 12/2017 Holt
2017/0354551 A1 12/2017 Gawley et al.
2017/0367873 A1 12/2017 Grannum
2018/0002075 A1 1/2018 Lee
2018/0008451 A1 1/2018 Stroebech
2018/0008804 A1 1/2018 Laniado
2018/0021218 A1 1/2018 Brosch et al.
2018/0028349 A1 2/2018 Newton et al.
2018/0037384 A1 2/2018 Archeny et al.
2018/0049910 A1 2/2018 Newton
2018/0064572 A1 3/2018 Wiltshire
2018/0104131 A1 4/2018 Killian
2018/0127187 A1 5/2018 Sewell
2018/0193215 A1 7/2018 Davies et al.
2018/0200101 A1 7/2018 Su
2018/0221216 A1 8/2018 Benz et al.
2018/0228642 A1* 8/2018 Davis ...................... A61F 5/451
2018/0256384 A1 9/2018 Kasirye
2018/0271694 A1 9/2018 Fernandez et al.
2018/0317892 A1 11/2018 Catlin
2018/0325748 A1 11/2018 Sharma et al.
2019/0001030 A1 1/2019 Braga et al.
2019/0021899 A1 1/2019 Vlet
2019/0038451 A1 2/2019 Harvie
2019/0046102 A1 2/2019 Kushnir et al.
2019/0059938 A1 2/2019 Holsten
2019/0091059 A1 3/2019 Gabriel
2019/0100362 A1 4/2019 Meyers et al.
2019/0133126 A1 5/2019 Modak et al.
2019/0133814 A1 5/2019 Tammen et al.
2019/0142624 A1 5/2019 Sanchez et al.
2019/0224036 A1 7/2019 Sanchez et al.
2019/0226189 A1 7/2019 Braxton
2019/0240079 A1 8/2019 Tul
2019/0247222 A1 8/2019 Ecklund et al.
2019/0247223 A1 8/2019 Brun et al.
2019/0247623 A1 8/2019 Helm et al.
2019/0282391 A1 9/2019 Johannes et al.
2019/0314189 A1 10/2019 Acosta
2019/0314190 A1 10/2019 Sanchez et al.
2019/0321587 A1 10/2019 Mcmenamin et al.
2019/0344934 A1 11/2019 Faerber et al.
2019/0365303 A1 12/2019 Bullington et al.
2019/0365307 A1 12/2019 Laing et al.
2019/0365561 A1 12/2019 Newton et al.
2019/0374373 A1 12/2019 Joh
2020/0008985 A1 1/2020 Nguyen et al.
2020/0016012 A1 1/2020 Dutkiewicz
2020/0030595 A1 1/2020 Boukidjian et al.
2020/0046544 A1 2/2020 Godinez et al.
2020/0055638 A1 2/2020 Lau et al.
2020/0070392 A1 3/2020 Huber et al.
2020/0085609 A1 3/2020 Schelch et al.
2020/0085610 A1 3/2020 Cohn et al.
2020/0086090 A1 3/2020 Von Weymarn-schärli et al.
2020/0107518 A1 4/2020 Hiroshima et al.
2020/0129322 A1 4/2020 Leuckel
2020/0171217 A9 6/2020 Braga et al.
2020/0179177 A1 6/2020 Erdem et al.
2020/0187918 A1 6/2020 Wiygul
2020/0206015 A1 7/2020 Langer
2020/0206039 A1 7/2020 Mclain
2020/0214910 A1 7/2020 Varona et al.
2020/0216898 A1 7/2020 Hubbell
2020/0216989 A1 7/2020 Kinugasa et al.
2020/0229964 A1 7/2020 Staali et al.
2020/0231343 A1 7/2020 Freedman et al.
2020/0232841 A1 7/2020 Satish et al.
2020/0246172 A1 8/2020 Ho
2020/0246203 A1 8/2020 Tulk et al.
2020/0255189 A1 8/2020 Liu
2020/0261280 A1 8/2020 Heyman
2020/0276046 A1 9/2020 Staali et al.
2020/0306075 A1 10/2020 Newton et al.
2020/0315837 A1 10/2020 Radl et al.
2020/0315838 A1 10/2020 Eckert
2020/0315872 A1 10/2020 Viens et al.
2020/0315874 A1 10/2020 Viens et al.
2020/0331672 A1 10/2020 Bertram et al.
2020/0345332 A1 11/2020 Duval
2020/0353135 A1 11/2020 Gregory et al.
2020/0367677 A1 11/2020 Silsby et al.
2020/0369444 A1 11/2020 Silsby et al.
2020/0375781 A1 12/2020 Staali et al.
2020/0375810 A1 12/2020 Carlin et al.
2020/0384242 A1 12/2020 Havard et al.
2020/0385179 A1 12/2020 Mccourt
2020/0390591 A1 12/2020 Glithero et al.
2020/0390592 A1 12/2020 Merrill
2020/0405521 A1 12/2020 Glasroe
2021/0008771 A1 1/2021 Huber et al.
2021/0009323 A1 1/2021 Markarian et al.
2021/0020072 A1 1/2021 Moehring et al.
2021/0023279 A1 1/2021 Radl et al.
2021/0059853 A1 3/2021 Davis et al.
2021/0061523 A1 3/2021 Bytheway
2021/0069005 A1 3/2021 Sanchez et al.
2021/0069008 A1 3/2021 Blabas et al.
2021/0069009 A1 3/2021 Im
2021/0069030 A1 3/2021 Nishikawa et al.
2021/0077993 A1 3/2021 Nazareth et al.
2021/0113749 A1 4/2021 Radl et al.
2021/0121318 A1 4/2021 Pinlac
2021/0137724 A1 5/2021 Ecklund et al.
2021/0138190 A1 5/2021 Erbey et al.
2021/0154055 A1 5/2021 Mllarreal
2021/0170079 A1 6/2021 Radl et al.
2021/0178390 A1 6/2021 Oueslati et al.
2021/0186742 A1 6/2021 Newton et al.
2021/0186744 A1 6/2021 Spector
2021/0211568 A1 7/2021 Zhou et al.
2021/0212865 A1 7/2021 Wallajapet et al.

(56) References Cited

U.S. PATENT DOCUMENTS

| | | | |
|---|---|---|---|
| 2021/0220162 | A1 | 7/2021 | Jamison |
| 2021/0220163 | A1 | 7/2021 | Mayrand |
| 2021/0228400 | A1 | 7/2021 | Glithero |
| 2021/0228401 | A1 | 7/2021 | Becker et al. |
| 2021/0228795 | A1 | 7/2021 | Hughett et al. |
| 2021/0229877 | A1 | 7/2021 | Ragias et al. |
| 2021/0236323 | A1 | 8/2021 | Austermann et al. |
| 2021/0236324 | A1 | 8/2021 | Sweeney |
| 2021/0251814 | A1 | 8/2021 | Jönegren et al. |
| 2021/0267787 | A1 | 9/2021 | Nazemi |
| 2021/0275343 | A1 | 9/2021 | Sanchez et al. |
| 2021/0275344 | A1 | 9/2021 | Wing |
| 2021/0290454 | A1 | 9/2021 | Yamada |
| 2021/0315726 | A1 | 10/2021 | Lin |
| 2021/0315727 | A1 | 10/2021 | Jiang |
| 2021/0353449 | A1 | 11/2021 | Sharma et al. |
| 2021/0353450 | A1 | 11/2021 | Sharma et al. |
| 2021/0361469 | A1 | 11/2021 | Liu et al. |
| 2021/0369495 | A1 | 12/2021 | Cheng et al. |
| 2021/0386925 | A1 | 12/2021 | Hartwell et al. |
| 2021/0393433 | A1 | 12/2021 | Godinez et al. |
| 2022/0023091 | A1 | 1/2022 | Ecklund et al. |
| 2022/0026546 | A1 | 1/2022 | Aono et al. |
| 2022/0031290 | A1 | 2/2022 | Weed |
| 2022/0031523 | A1 | 2/2022 | Pierpoint |
| 2022/0039995 | A1 | 2/2022 | Johannes et al. |
| 2022/0047410 | A1 | 2/2022 | Walthall |
| 2022/0062025 | A1 | 3/2022 | Shields et al. |
| 2022/0062027 | A1 | 3/2022 | Mitchell et al. |
| 2022/0062028 | A1 | 3/2022 | Mitchell et al. |
| 2022/0062029 | A1 | 3/2022 | Johannes et al. |
| 2022/0066825 | A1 | 3/2022 | Saraf et al. |
| 2022/0071811 | A1 | 3/2022 | Cheng et al. |
| 2022/0071826 | A1 | 3/2022 | Kulkarni et al. |
| 2022/0104965 | A1 | 4/2022 | Vaninetti et al. |
| 2022/0104976 | A1 | 4/2022 | Hoeger et al. |
| 2022/0104981 | A1 | 4/2022 | Jones |
| 2022/0117773 | A1 | 4/2022 | Davis et al. |
| 2022/0117774 | A1 | 4/2022 | Meyer et al. |
| 2022/0117775 | A1 | 4/2022 | Jones et al. |
| 2022/0118165 | A1 | 4/2022 | Knapp et al. |
| 2022/0133524 | A1 | 5/2022 | Davis |
| 2022/0151817 | A1 | 5/2022 | Mann |
| 2022/0160949 | A1 | 5/2022 | Simiele et al. |
| 2022/0168159 | A1 | 6/2022 | Triado et al. |
| 2022/0193312 | A1 | 6/2022 | Lee et al. |
| 2022/0211536 | A1 | 7/2022 | Johannes et al. |
| 2022/0218510 | A1 | 7/2022 | Metzger et al. |
| 2022/0229053 | A1 | 7/2022 | Levin et al. |
| 2022/0241106 | A1 | 8/2022 | Johannes et al. |
| 2022/0247407 | A1 | 8/2022 | Yamamoto et al. |
| 2022/0248836 | A1 | 8/2022 | Cagle et al. |
| 2022/0257407 | A1 | 8/2022 | Johannes et al. |
| 2022/0265460 | A1 | 8/2022 | Coker |
| 2022/0265462 | A1 | 8/2022 | Alder et al. |
| 2022/0270711 | A1 | 8/2022 | Feala et al. |
| 2022/0273482 | A1 | 9/2022 | Johannes et al. |
| 2022/0280357 | A1 | 9/2022 | Jagannathan et al. |
| 2022/0280710 | A1 | 9/2022 | Agrawal et al. |
| 2022/0287689 | A1 | 9/2022 | Johannes |
| 2022/0287867 | A1 | 9/2022 | Jones et al. |
| 2022/0287868 | A1 | 9/2022 | Garvey et al. |
| 2022/0296408 | A1 | 9/2022 | Evans et al. |
| 2022/0305191 | A1 | 9/2022 | Joseph et al. |
| 2022/0313222 | A1 | 10/2022 | Austermann et al. |
| 2022/0313474 | A1 | 10/2022 | Kriscovich et al. |
| 2022/0331170 | A1 | 10/2022 | Erdem et al. |
| 2022/0339023 | A1 | 10/2022 | Davis et al. |
| 2022/0339024 | A1 | 10/2022 | Johannes et al. |
| 2022/0354685 | A1 | 11/2022 | Davis et al. |
| 2022/0362049 | A1 | 11/2022 | Austermann et al. |
| 2022/0370231 | A1 | 11/2022 | Wang et al. |
| 2022/0370234 | A1 | 11/2022 | Hughett et al. |
| 2022/0370235 | A1 | 11/2022 | Johannes et al. |
| 2022/0370237 | A1 | 11/2022 | Parmar et al. |
| 2022/0387001 | A1 | 12/2022 | Askenazi et al. |
| 2022/0387693 | A1 | 12/2022 | Bannwart et al. |
| 2022/0395390 | A1 | 12/2022 | Brooks |
| 2022/0395391 | A1 | 12/2022 | Saunders et al. |
| 2022/0401252 | A1 | 12/2022 | Warren |
| 2022/0409419 | A1 | 12/2022 | Garvey et al. |
| 2022/0409422 | A1 | 12/2022 | Schneider et al. |
| 2023/0018845 | A1 | 1/2023 | Lee |
| 2023/0020563 | A1 | 1/2023 | Sharma et al. |
| 2023/0031640 | A1 | 2/2023 | Hughett et al. |
| 2023/0037159 | A1 | 2/2023 | Brennan et al. |
| 2023/0049924 | A1 | 2/2023 | Johannes et al. |
| 2023/0052238 | A1 | 2/2023 | Oluwasogo |
| 2023/0062994 | A1 | 3/2023 | Ecklund et al. |
| 2023/0070347 | A1 | 3/2023 | Watson et al. |
| 2023/0073708 | A1 | 3/2023 | Xu et al. |
| 2023/0089032 | A1 | 3/2023 | Hughett et al. |
| 2023/0091118 | A1 | 3/2023 | Watson |
| 2023/0099821 | A1 | 3/2023 | Radl et al. |
| 2023/0099991 | A1 | 3/2023 | Bianchi et al. |
| 2023/0105001 | A1 | 4/2023 | Whittome et al. |
| 2023/0110577 | A1 | 4/2023 | Choi |
| 2023/0138269 | A1 | 5/2023 | Abdelal et al. |
| 2023/0145365 | A1 | 5/2023 | Martin et al. |
| 2023/0155253 | A1 | 5/2023 | Mn et al. |
| 2023/0190511 | A1 | 6/2023 | Sharma et al. |
| 2023/0210504 | A1 | 7/2023 | Kuroda et al. |
| 2023/0210685 | A1 | 7/2023 | Fallows et al. |
| 2023/0218426 | A1 | 7/2023 | Hughett |
| 2023/0240884 | A1 | 8/2023 | Davis et al. |
| 2023/0248562 | A1 | 8/2023 | Sanchez et al. |
| 2023/0248564 | A1 | 8/2023 | Mann et al. |
| 2023/0255812 | A1 | 8/2023 | Sanchez et al. |
| 2023/0255813 | A1 | 8/2023 | Sanchez et al. |
| 2023/0255815 | A1 | 8/2023 | Newton |
| 2023/0263650 | A1 | 8/2023 | Sanchez et al. |
| 2023/0263655 | A1 | 8/2023 | Johannes et al. |
| 2023/0277360 | A1 | 9/2023 | Lambert et al. |
| 2023/0277362 | A1 | 9/2023 | Davis et al. |
| 2023/0285178 | A1 | 9/2023 | Sanchez et al. |
| 2023/0293339 | A1 | 9/2023 | James |
| 2023/0301846 | A1 | 9/2023 | Greenwood |
| 2023/0355423 | A1 | 11/2023 | Stevenson et al. |
| 2023/0389900 | A1 | 12/2023 | Xie et al. |
| 2023/0404791 | A1 | 12/2023 | Ecklund et al. |
| 2024/0008444 | A1 | 1/2024 | Su et al. |
| 2024/0009023 | A1 | 1/2024 | Johannes et al. |
| 2024/0024170 | A1 | 1/2024 | Scott |
| 2024/0033148 | A1 | 2/2024 | Gordon et al. |
| 2024/0041638 | A1 | 2/2024 | Johannes et al. |
| 2024/0058160 | A1 | 2/2024 | Young Joyner et al. |
| 2024/0058161 | A1 | 2/2024 | Ulreich et al. |
| 2024/0058520 | A1 | 2/2024 | Yin et al. |
| 2024/0065881 | A1 | 2/2024 | Kuroda et al. |
| 2024/0082044 | A1 | 3/2024 | Nguyen et al. |
| 2024/0099874 | A1 | 3/2024 | Sanchez et al. |
| 2024/0108268 | A1 | 4/2024 | Woodard et al. |
| 2024/0110318 | A1 | 4/2024 | Bendt et al. |
| 2024/0122773 | A1 | 4/2024 | Nguyen et al. |
| 2024/0123134 | A1 | 4/2024 | Kharkar et al. |
| 2024/0130885 | A1 | 4/2024 | Young Joyner et al. |
| 2024/0148539 | A1 | 5/2024 | Austermann et al. |
| 2024/0156633 | A1 | 5/2024 | Fallows et al. |
| 2024/0164935 | A1 | 5/2024 | Newton |
| 2024/0252343 | A1 | 8/2024 | Voda |
| 2024/0261131 | A1 | 8/2024 | Garvey et al. |
| 2024/0268986 | A1 | 8/2024 | Barnes et al. |
| 2024/0268989 | A1 | 8/2024 | Martin et al. |
| 2024/0268991 | A1 | 8/2024 | Davis |
| 2024/0269027 | A1 | 8/2024 | Tourchak et al. |
| 2024/0285425 | A1 | 8/2024 | Donohoe et al. |
| 2024/0325190 | A1 | 10/2024 | Minchew et al. |
| 2024/0358539 | A1 | 10/2024 | Gallup |
| 2024/0358542 | A1 | 10/2024 | Richardson et al. |
| 2024/0374414 | A1 | 11/2024 | Richardson et al. |
| 2025/0009552 | A1 | 1/2025 | Blabas et al. |
| 2025/0073055 | A1 | 3/2025 | Ecklund et al. |

(56) References Cited

U.S. PATENT DOCUMENTS

| | | | |
|---|---|---|---|
| 2025/0107920 A1 | 4/2025 | Fallows et al. |
| 2025/0107921 A1 | 4/2025 | Sanchez et al. |

FOREIGN PATENT DOCUMENTS

| | | | |
|---|---|---|---|
| AU | 2022349367 | A1 | 4/2024 |
| CA | 2165286 | C | 9/1999 |
| CA | 2335223 | A1 | 1/2000 |
| CA | 2354132 | A1 | 6/2000 |
| CA | 2359091 | C | 9/2003 |
| CA | 2488867 | C | 8/2007 |
| CA | 3050918 | A1 | 8/2018 |
| CA | 3098571 | A1 | 11/2019 |
| CA | 3144181 | A1 | 1/2021 |
| CA | 3188651 | A1 | 7/2023 |
| CN | 2269203 | Y | 12/1997 |
| CN | 1332620 | A | 1/2002 |
| CN | 1434693 | A | 8/2003 |
| CN | 1533755 | A | 10/2004 |
| CN | 1579348 | A | 2/2005 |
| CN | 1602825 | A | 4/2005 |
| CN | 1638708 | A | 7/2005 |
| CN | 1720888 | A | 1/2006 |
| CN | 2936204 | Y | 8/2007 |
| CN | 101262836 | A | 9/2008 |
| CN | 101522148 | A | 9/2009 |
| CN | 102159159 | A | 8/2011 |
| CN | 202184840 | U | 4/2012 |
| CN | 102481441 | A | 5/2012 |
| CN | 202463712 | U | 10/2012 |
| CN | 202950810 | U | 5/2013 |
| CN | 103533968 | A | 1/2014 |
| CN | 103717180 | A | 4/2014 |
| CN | 204562697 | U | 8/2015 |
| CN | 105411783 | A | 3/2016 |
| CN | 105451693 | A | 3/2016 |
| CN | 105534632 | A | 5/2016 |
| CN | 106132360 | A | 11/2016 |
| CN | 205849719 | U | 1/2017 |
| CN | 205924282 | U | 2/2017 |
| CN | 106726089 | A | 5/2017 |
| CN | 107847384 | A | 3/2018 |
| CN | 107920912 | A | 4/2018 |
| CN | 108420590 | A | 8/2018 |
| CN | 209285902 | U | 8/2019 |
| CN | 110381883 | A | 10/2019 |
| CN | 211198839 | U | 8/2020 |
| CN | 111991136 | A | 11/2020 |
| CN | 112022488 | A | 12/2020 |
| CN | 212234893 | U | 12/2020 |
| CN | 212466312 | U | 2/2021 |
| CN | 112566550 | A | 3/2021 |
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |
| DE | 79818 | C | 10/1893 |
| DE | 1516466 | A1 | 6/1969 |
| DE | 2721330 | A1 | 11/1977 |
| DE | 2742298 | A1 | 3/1978 |
| DE | 9407554 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 102005037762 | B3 | 9/2006 |
| DE | 102011103783 | A1 | 12/2012 |
| DE | 102012112818 | A1 | 6/2014 |
| DE | 202015104597 | U1 | 7/2016 |
| DE | 102018118570 | A1 | 2/2020 |
| DE | 102020121462 | B3 | 1/2022 |
| DK | 9600118 | U3 | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0220962 | A1 | 5/1987 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0483730 | A1 | 5/1992 |
| EP | 0610638 | A1 | 8/1994 |
| EP | 0613355 | A1 | 9/1994 |
| EP | 0680296 | A1 | 11/1995 |
| EP | 0711536 | A1 | 5/1996 |
| EP | 0613355 | B1 | 1/1997 |
| EP | 0787472 | A1 | 8/1997 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3777801 | A1 | 2/2021 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3569205 | B1 | 6/2023 |
| EP | 4218702 | A1 | 8/2023 |
| EP | 4382082 | A2 | 6/2024 |
| EP | 4445881 | A2 | 10/2024 |
| EP | 4464288 | A2 | 11/2024 |
| EP | 4527361 | A2 | 3/2025 |
| FR | 2826704 | A1 | 1/2003 |
| GB | 871820 | A | 7/1961 |
| GB | 873045 | A | 7/1961 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2415386 | A | 12/2005 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58188016 | U | 12/1983 |

(56) References Cited

FOREIGN PATENT DOCUMENTS

| | | | | |
|---|---|---|---|---|
| JP | S59118161 | A | | 7/1984 |
| JP | S61502100 | A | | 9/1986 |
| JP | S63107780 | U | | 7/1988 |
| JP | H0267530 | A | | 3/1990 |
| JP | H02103871 | A | | 4/1990 |
| JP | H02131422 | A | | 5/1990 |
| JP | H02131422 | U | | 11/1990 |
| JP | H0460220 | A | | 2/1992 |
| JP | H0515928 | U | | 3/1993 |
| JP | H05123349 | A | | 5/1993 |
| JP | H05123350 | A | | 5/1993 |
| JP | H0626264 | U | | 4/1994 |
| JP | 3087938 | B2 | | 10/1995 |
| JP | H085630 | A | | 1/1996 |
| JP | H08117271 | A | | 5/1996 |
| JP | 2686634 | B2 | | 12/1997 |
| JP | H1040141 | A | | 2/1998 |
| JP | H10225430 | A | | 8/1998 |
| JP | H11113946 | A | | 4/1999 |
| JP | H11290365 | A | | 10/1999 |
| JP | 2000116690 | A | | 4/2000 |
| JP | 2000152953 | A | | 6/2000 |
| JP | 2000185068 | A | | 7/2000 |
| JP | 2000225139 | A | | 8/2000 |
| JP | 2001054531 | A | | 2/2001 |
| JP | 2001070331 | A | | 3/2001 |
| JP | 2001224616 | A | | 8/2001 |
| JP | 2001276107 | A | | 10/2001 |
| JP | 2001276108 | A | | 10/2001 |
| JP | 2002028173 | A | | 1/2002 |
| JP | 2002502667 | A | | 1/2002 |
| JP | 2002102285 | A | | 4/2002 |
| JP | 2003038563 | A | | 2/2003 |
| JP | 2003505152 | A | | 2/2003 |
| JP | 2003126242 | A | | 5/2003 |
| JP | 2003180722 | A | | 7/2003 |
| JP | 2003227004 | A | | 8/2003 |
| JP | 2003528691 | A | | 9/2003 |
| JP | 2004057578 | A | | 2/2004 |
| JP | 2004130056 | A | | 4/2004 |
| JP | 2004267400 | A | | 9/2004 |
| JP | 2004267530 | A | | 9/2004 |
| JP | 2005052219 | A | | 3/2005 |
| JP | 2005066011 | A | | 3/2005 |
| JP | 2005066325 | A | | 3/2005 |
| JP | 2005102978 | A | | 4/2005 |
| JP | 2005518237 | A | | 6/2005 |
| JP | 2005518901 | A | | 6/2005 |
| JP | 3749097 | B2 | | 2/2006 |
| JP | 2006026108 | A | | 2/2006 |
| JP | 3123547 | B2 | | 6/2006 |
| JP | 2006136491 | A | | 6/2006 |
| JP | 2006136492 | A | | 6/2006 |
| JP | 2006204868 | A | | 8/2006 |
| JP | 2007044494 | A | | 2/2007 |
| JP | 3132659 | B2 | | 5/2007 |
| JP | 2007209687 | A | | 8/2007 |
| JP | 2007259898 | A | | 10/2007 |
| JP | 4039641 | B2 | | 11/2007 |
| JP | 2008005975 | A | | 1/2008 |
| JP | 2009509570 | A | | 3/2009 |
| JP | 2009165887 | A | | 7/2009 |
| JP | 2009525776 | A | | 7/2009 |
| JP | 2010504150 | A | | 2/2010 |
| JP | 2010058795 | A | | 3/2010 |
| JP | 2010081981 | A | | 4/2010 |
| JP | 2010166954 | A | | 8/2010 |
| JP | 2010536439 | A | | 12/2010 |
| JP | 2011500225 | A | | 1/2011 |
| JP | 2011030962 | A | | 2/2011 |
| JP | 4640772 | B2 | | 3/2011 |
| JP | 4747166 | B2 | | 5/2011 |
| JP | 2011087823 | A | | 5/2011 |
| JP | 4801218 | B1 | | 8/2011 |
| JP | 2011522584 | A | | 8/2011 |
| JP | 2011202664 | A | | 10/2011 |
| JP | 2011218130 | A | | 11/2011 |
| JP | 2011224070 | A | | 11/2011 |
| JP | 3175719 | U | | 4/2012 |
| JP | 2012523869 | A | | 10/2012 |
| JP | 2013238608 | A | | 11/2013 |
| JP | 2014521960 | A | | 8/2014 |
| JP | 2015092945 | A | | 5/2015 |
| JP | 2015513678 | A | | 5/2015 |
| JP | 3198994 | B2 | | 7/2015 |
| JP | 2015221390 | A | | 12/2015 |
| JP | 2016521191 | A | | 7/2016 |
| JP | 2017014698 | A | | 1/2017 |
| JP | 3208707 | U | | 2/2017 |
| JP | 3209321 | U | | 3/2017 |
| JP | 2017070400 | A | | 4/2017 |
| JP | 2017512603 | A | | 5/2017 |
| JP | 2017127596 | A | | 7/2017 |
| JP | 2017201272 | A | | 11/2017 |
| JP | 2019010375 | A | | 1/2019 |
| JP | 2019076342 | A | | 5/2019 |
| JP | 2019525811 | A | | 9/2019 |
| JP | 2019170942 | A | | 10/2019 |
| JP | 2019533492 | A | | 11/2019 |
| JP | 2020510464 | A | | 4/2020 |
| JP | 2020520775 | A | | 7/2020 |
| JP | 2020124425 | A | | 8/2020 |
| JP | 2021007472 | A | | 1/2021 |
| JP | 2021041145 | A | | 3/2021 |
| JP | 2021074491 | A | | 5/2021 |
| JP | 2021120686 | A | | 8/2021 |
| JP | 2021520952 | A | | 8/2021 |
| JP | 2021522009 | A | | 8/2021 |
| JP | 2021522013 | A | | 8/2021 |
| JP | 2021522019 | A | | 8/2021 |
| JP | 7129493 | B2 | | 8/2022 |
| JP | 2022554252 | A | | 12/2022 |
| JP | 2023532132 | A | | 7/2023 |
| KR | 200290061 | Y1 | | 9/2002 |
| KR | 20030047451 | A | | 6/2003 |
| KR | 20080005516 | A | | 1/2008 |
| KR | 20090072069 | A | | 7/2009 |
| KR | 20090104426 | A | * | 10/2009 |
| KR | 20090110359 | A | | 10/2009 |
| KR | 20120005922 | A | | 1/2012 |
| KR | 20140039485 | A | | 4/2014 |
| KR | 101432639 | B1 | | 8/2014 |
| KR | 20180106659 | A | | 10/2018 |
| KR | 20180108774 | A | | 10/2018 |
| KR | 20230034343 | A | | 3/2023 |
| PT | 2068717 | E | | 6/2013 |
| SE | 505542 | C2 | | 9/1997 |
| TW | 408207 | B | | 10/2000 |
| WO | 8101957 | A1 | | 7/1981 |
| WO | 8804558 | A1 | | 6/1988 |
| WO | 9104714 | A2 | | 4/1991 |
| WO | 9104714 | A3 | | 6/1991 |
| WO | 9220299 | A3 | | 2/1993 |
| WO | 9303690 | A1 | | 3/1993 |
| WO | 9307839 | A1 | | 4/1993 |
| WO | 9309736 | A2 | | 5/1993 |
| WO | 9309736 | A3 | | 6/1993 |
| WO | 9416914 | A1 | | 8/1994 |
| WO | 9514448 | A2 | | 6/1995 |
| WO | 9600096 | A1 | | 1/1996 |
| WO | 9634636 | A1 | | 11/1996 |
| WO | 9817211 | A1 | | 4/1998 |
| WO | 9830336 | A1 | | 7/1998 |
| WO | 0000112 | A1 | | 1/2000 |
| WO | 0000113 | A1 | | 1/2000 |
| WO | 0025651 | A1 | | 5/2000 |
| WO | 0033773 | A1 | | 6/2000 |
| WO | 0057784 | A1 | | 10/2000 |
| WO | 0069377 | A1 | | 11/2000 |
| WO | 0079497 | A1 | | 12/2000 |
| WO | 0145618 | A1 | | 6/2001 |
| WO | 0145621 | A1 | | 6/2001 |
| WO | 02094160 | A1 | | 11/2002 |
| WO | 03013967 | A1 | | 2/2003 |

(56) References Cited

FOREIGN PATENT DOCUMENTS

| | | | |
|---|---|---|---|
| WO | 03015671 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005051252 | A1 | 6/2005 |
| WO | 2005060558 | A2 | 7/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007134608 | A2 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012020506 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017100511 | A1 | 6/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018235026 | A1 | 12/2018 |
| WO | 2018235065 | A1 | 12/2018 |
| WO | 2019004404 | A1 | 1/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020033752 | A1 | 2/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016056 | A1 | 1/2021 |
| WO | 2021016300 | A1 | 1/2021 |
| WO | 2021025919 | A1 | 2/2021 |
| WO | 2021034886 | A1 | 2/2021 |

(56) References Cited

FOREIGN PATENT DOCUMENTS

WO 2021041123 A1 3/2021
WO 2021046501 A1 3/2021
WO 2021086868 A1 5/2021
WO 2021094352 A1 5/2021
WO 2021094639 A1 5/2021
WO 2021097067 A1 5/2021
WO 2021102296 A1 5/2021
WO 2021107025 A1 6/2021
WO 2021138411 A1 7/2021
WO 2021138414 A1 7/2021
WO 2021154686 A1 8/2021
WO 2021155206 A1 8/2021
WO 2021170075 A1 9/2021
WO 2021173436 A1 9/2021
WO 2021188817 A1 9/2021
WO 2021195384 A1 9/2021
WO 2021205995 A1 10/2021
WO 2021207621 A1 10/2021
WO 2021211568 A1 10/2021
WO 2021211801 A1 10/2021
WO 2021211914 A1 10/2021
WO 2021216419 A1 10/2021
WO 2021216422 A1 10/2021
WO 2021231532 A1 11/2021
WO 2021247523 A1 12/2021
WO 2021257202 A1 12/2021
WO 2022006256 A1 1/2022
WO 2022029662 A1 2/2022
WO 2022031943 A1 2/2022
WO 2022035745 A1 2/2022
WO 2022051220 A1 3/2022
WO 2022051360 A1 3/2022
WO 2022054613 A1 3/2022
WO 2022066704 A1 3/2022
WO 2022067392 A1 4/2022
WO 2022069950 A1 4/2022
WO 2022071429 A1 4/2022
WO 2022076322 A1 4/2022
WO 2022076427 A2 4/2022
WO 2022086898 A1 4/2022
WO 2022090199 A1 5/2022
WO 2022098536 A1 5/2022
WO 2022099087 A1 5/2022
WO 2022101999 A1 5/2022
WO 2022115692 A1 6/2022
WO 2022125685 A1 6/2022
WO 2022140545 A1 6/2022
WO 2022145231 A1 7/2022
WO 2022150290 A1 7/2022
WO 2022150360 A1 7/2022
WO 2022150463 A1 7/2022
WO 2022159392 A1 7/2022
WO 2022170182 A1 8/2022
WO 2022173803 A1 8/2022
WO 2022182385 A1 9/2022
WO 2022187152 A1 9/2022
WO 2022192188 A1 9/2022
WO 2022192347 A1 9/2022
WO 2022204000 A1 9/2022
WO 2022216776 A1 10/2022
WO 2022222030 A1 10/2022
WO WO-2022216507 A1 * 10/2022 ........... A61F 5/4401
WO 2022251184 A1 12/2022
WO 2022251425 A1 12/2022
WO 2022271783 A1 12/2022
WO 2023286058 A1 1/2023
WO 2023014639 A1 2/2023
WO 2023014641 A1 2/2023
WO 2023018475 A2 2/2023
WO 2023018656 A1 2/2023
WO 2023018657 A1 2/2023
WO 2023023777 A1 3/2023
WO 2023034139 A1 3/2023
WO 2023034453 A1 3/2023
WO 2023038945 A1 3/2023
WO 2023038950 A1 3/2023
WO 2023049109 A1 3/2023
WO 2023049156 A1 3/2023
WO 2023049175 A1 3/2023
WO 2023086394 A1 5/2023
WO 2023149884 A1 8/2023
WO 2023149902 A1 8/2023
WO 2023149903 A1 8/2023
WO 2023154390 A1 8/2023
WO 2023163725 A1 8/2023
WO 2023191764 A1 10/2023
WO 2023244238 A1 12/2023
WO 2024043871 A1 2/2024
WO 2024058788 A1 3/2024
WO 2024253655 A1 12/2024
WO 2025034959 A1 2/2025
WO 2025038087 A1 2/2025
WO 2025038088 A1 2/2025
WO 2025071622 A1 4/2025

OTHER PUBLICATIONS

Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Oct. 26, 2022.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/450,864 mailed on Mar. 21, 2024.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/662,700 mailed Jan. 30, 2023.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 18/164,800 mailed Feb. 12, 2024.
Communication of Notice of Opposition of European Application No. 17807547.9 mailed Jan. 5, 2024.

(56) References Cited

OTHER PUBLICATIONS

Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowance for U.S. Appl. No. 17/657,474 mailed Mar. 13, 2024.
Final Office Action for U.S. Appl. No. 16/245,726 mailed Nov. 25, 2022.
Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 10, 2023.
Final Office Action for U.S. Appl. No. 16/433,773 mailed Oct. 25, 2022.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/478,180 mailed May 31, 2023.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/179,116 mailed Oct. 31, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/446,654 mailed Jan. 31, 2024.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/662,700 mailed Sep. 30, 2022.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 18/139,523 mailed Dec. 22, 2023.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/US2023/031433 mailed Mar. 4, 2024.
International Search Report and Written Opinion from International Application No. PCT/IB2021/057173 mailed Nov. 5, 2021.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015781 mailed May 6, 2022.
International Search Report and Written Opinion from International Application No. PCT/US2022/018159 mailed Dec. 12, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.

(56) References Cited

OTHER PUBLICATIONS

International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/031740 mailed Mar. 4, 2024.
Issue Notification for U.S. Appl. No. 16/245,726 mailed Oct. 18, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/461,036 mailed Oct. 11, 2023.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Apr. 11, 2023.
Non-Final Office Action for U.S. Appl. No. 16/433,773 mailed Feb. 26, 2024.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,258 mailed Apr. 26, 2023.
Non-Final Office Action for U.S. Appl. No. 16/478,180 mailed Dec. 20, 2022.
Non-Final Office Action for U.S. Appl. No. 16/478,180 mailed Nov. 7, 2023.
Non-Final Office Action for U.S. Appl. No. 16/904,868 mailed Mar. 12, 2024.
Non-Final Office Action for U.S. Appl. No. 16/904,868 mailed Mar. 15, 2023.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,585 mailed Mar. 29, 2023.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/444,792 mailed Nov. 17, 2023.
Non-Final Office Action for U.S. Appl. No. 17/446,256 mailed Apr. 13, 2023.
Non-Final Office Action for U.S. Appl. No. 17/446,256 mailed Feb. 13, 2024.
Non-Final Office Action for U.S. Appl. No. 17/446,654 mailed Sep. 8, 2023.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,345 mailed Jan. 17, 2024.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/453,560 mailed Oct. 16, 2023.
Non-Final Office Action for U.S. Appl. No. 17/501,591 mailed Apr. 25, 2023.
Non-Final Office Action for U.S. Appl. No. 17/597,673 mailed Mar. 20, 2024.
Non-Final Office Action for U.S. Appl. No. 17/645,821 mailed Oct. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/653,137 mailed Jan. 18, 2024.
Non-Final Office Action for U.S. Appl. No. 17/655,464 mailed Mar. 14, 2023.
Non-Final Office Action for U.S. Appl. No. 17/655,464 mailed Mar. 26, 2024.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 18/164,800 mailed Mar. 22, 2024.
Non-Final Office Action for U.S. Appl. No. 18/198,464 mailed Dec. 7, 2023.

(56) References Cited

OTHER PUBLICATIONS

Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 16/449,039 mailed Dec. 15, 2022.
Notice of Allowance for U.S. Appl. No. 16/899,956 mailed Dec. 1, 2022.
Notice of Allowance for U.S. Appl. No. 17/051,550 mailed Feb. 7, 2024.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/326,980 mailed Jan. 29, 2024.
Notice of Allowance for U.S. Appl. No. 17/453,560 mailed Jan. 31, 2024.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/657,474 mailed Mar. 5, 2024.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/299,788 mailed Jul. 24, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 17/667,097 mailed Mar. 20, 2024.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
Text Messages to Lorena Eckert Re Prototype PureWick Holder dated Apr. 16, 2022.
U.S. Appl. No. 15/260,103, filed Sep. 8, 2016.
U.S. Appl. No. 17/444,792, filed Aug. 10, 2021.
U.S. Appl. No. 17/451,719, filed Oct. 19, 2021.
U.S. Appl. No. 17/664,487, filed May 23, 2022.
U.S. Appl. No. 17/996,064, filed Oct. 12, 2022.
U.S. Appl. No. 17/996,155 filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/249,577, filed Oct. 19, 2021.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/294,370, filed Feb. 1, 2024.
U.S. Appl. No. 18/294,403, filed Feb. 1, 2024.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 63/150,640, filed Feb. 18, 2021.
U.S. Appl. No. 63/308,190, filed Feb. 9, 2022.
U.S. Appl. No. 63/561,893, filed Dec. 11, 2023.
U.S. Appl. No. 63/596,012, filed Nov. 3, 2023.
U.S. Appl. No. 63/608,553, filed Dec. 11, 2023.
*PureWick Corporation* v. *Sage Products, LLC Transcripts* vol. 2, Mar. 29, 2022.
*PureWick Corporation* v. *Sage Products, LLC Transcripts* vol. 3, Mar. 30, 2022.
*PureWick Corporation* v. *Sage Products, LLC Transcripts* vol. 4, Mar. 31, 2022.
*PureWick Corporation* v. *Sage Products, LLC Transcripts* vol. 5, Apr. 1, 2022.
*PureWick Corporation* v. *Sage Products, LLC Transcripts* vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.

(56) References Cited

OTHER PUBLICATIONS

"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Merriam-Webster Dictionary, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, Mar./Apr. 1993, pp. 51-55.
Vinas, "A Solution For An Awkward—But Serious—Subject", http://www.aero-news.net/index.cfm?do=main.textpost&id=69ae2bb1-838b-4098-a7b5-7flbb2505688 last accessed Feb. 8, 2021.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/452,145 mailed Mar. 25, 2022.
Final Office Action for U.S. Appl. No. 16/478,180 mailed Jun. 22, 2022.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.

(56) References Cited

OTHER PUBLICATIONS

International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/012794 mailed May 3, 2022.
International Search Report and Written Opinion from International Application No. PCT/US2022/015471 mailed May 16, 2022.
International Search Report and Written Opinion from International Application No. PCT/US2022/016942 mailed Jun. 8, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 21, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.

(56) References Cited

OTHER PUBLICATIONS

Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/899,956 mailed Apr. 19, 2022.
Notice of Allowance for U.S. Appl. No. 16/899,956 mailed Dec. 29, 2021.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice of Allowance for U.S. Appl. No. 29/741,751 mailed Jun. 9, 2022.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/384,196, filed Dec. 19, 2016.
U.S. Appl. No. 15/611,587, filed Jun. 1, 2017.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914 filed May 25, 222.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.

(56) References Cited

OTHER PUBLICATIONS

U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,977, filed Jan. 30, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (Patent No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, Llc's Answer, Defenses, and Counterclaims To Plaintiff's Amended Complaint, Nov. 1, 2019.

(56) References Cited

OTHER PUBLICATIONS

Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml vol. Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
ALI , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.
Jagota , et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Macaulay , et al., "A Noninvasive Continence Management System: Development and Evaluation of a Novel Toileting Device for Women", The Wound, Ostomy and Continence Nurses Society, 2007, pp. 641-648.
Newman , et al., "The Urinary Incontinence Sourcebook", Petition for Interparties Review, 1997, 23 pages.
Newton , et al., "Measuring Safety, Effectiveness and Ease of Use of PureWick in the Management of Urinary Incontinence in Bedbound Women: Case Studies", Jan. 8, 2016, 11 pages.
PARMAR , "10 Finalists Chosen for Dare-to-Dream Medtech Design Challenge (PureWick)", Design Services, Nov. 10, 2014, 3 pages.
Parness , et al., "A microfabricated wedge-shaped adhesive array displaying gecko-like dynamic adhesion, directionality", J.R. Soc. Interface, 2009, pp. 1223-1232.
Purewick , "Incontinence Relief for Women", Presentation, Sep. 23, 2015, 7 pages.
Pytlik , "Super Absorbent Polymers", University of Buffalo.
Sachtman , "New Relief for Pilots? It Depends", Wired, 2008, 2 pages.
Tsipenyuk , et al., "Use of biomimetic hexagonal surface texture in friction against lubricated skin", Journal of The Royal Society—Interface, 2014, pp. 1-6.
Advisory Action for U.S. Appl. No. 16/478,180 mailed Sep. 21, 2022.
Final Office Action for U.S. Appl. No. 16/449,039 mailed Aug. 1, 2022.
Final Office Action for U.S. Appl. No. 16/452,258 mailed Jun. 14, 2022.
International Search Report and Written Opinion from International Application No. PCT/US2021/039866 mailed Oct. 7, 2021.
International Search Report and Written Opinion from International Application No. PCT/US2022/011421 mailed Jun. 13, 2022.
International Search Report and Written Opinion from International Application No. PCT/US2022/015492 mailed Apr. 26, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
Non-Final Office Action for U.S. Appl. No. 17/662,700 mailed Jul. 22, 2022.
Notice of Allowance for U.S. Appl. No. 16/899,956 mailed Aug. 10, 2022.
Notice of Allowance for U.S. Appl. No. 16/905,400 mailed Aug. 17, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.

(56) References Cited

OTHER PUBLICATIONS

U.S. Appl. No. 17/933,590, filed Sep. 20, 2022.
U.S. Appl. No. 62/967,158, filed Jan. 26, 2020.
U.S. Appl. No. 62/991,754, filed Mar. 19, 2020.
U.S. Appl. No. 63/241,328, filed Sep. 7, 2021.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/051,585 mailed Oct. 8, 2024.
Advisory Action for U.S. Appl. No. 17/444,792 mailed Jul. 8, 2024.
Advisory Action for U.S. Appl. No. 17/446,256 mailed Nov. 19, 2024.
Advisory Action for U.S. Appl. No. 17/446,654 mailed Apr. 15, 2024.
Advisory Action for U.S. Appl. No. 17/451,345 mailed Jul. 3, 2024.
Advisory Action for U.S. Appl. No. 17/645,821 mailed Jul. 2, 2024.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 17/808,354 mailed Jun. 12, 2024.
Advisory Action for U.S. Appl. No. 18/134,857 mailed Oct. 23, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/451,354 mailed Oct. 28, 2024.
Final Office Action for U.S. Appl. No. 17/597,673 mailed Oct. 22, 2024.
Final Office Action for U.S. Appl. No. 17/645,821 mailed Apr. 3, 2024.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/808,354 mailed Apr. 10, 2024.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/140,163 mailed Mar. 27, 2024.
Final Office Action for U.S. Appl. No. 18/164,800 mailed Oct. 22, 2024.
Final Office Acton for U.S. Appl. No. 17/595,747 mailed Dec. 12, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
Issue Notification for U.S. Appl. No. 16/369,676 mailed Oct. 2, 2024.
Issue Notification for U.S. Appl. No. 16/449,039 mailed Jun. 19, 2024.
Issue Notification for U.S. Appl. No. 16/452,145 mailed Oct. 23, 2024.
Issue Notification for U.S. Appl. No. 17/179,116 mailed Dec. 25, 2024.
Issue Notification for U.S. Appl. No. 17/326,980 mailed Jul. 10, 2024.
Issue Notification for U.S. Appl. No. 17/447,123 mailed Nov. 13, 2024.
Issue Notification for U.S. Appl. No. 17/448,811 mailed Jul. 3, 2024.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/657,474 mailed Jun. 19, 2024.
Issue Notification for U.S. Appl. No. 17/662,700 mailed Oct. 23, 2024.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/198,464 mailed Nov. 20, 2024.
Issue Notification for U.S. Appl. No. 18/389,009 mailed Dec. 18, 2024.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 17/378,015 mailed Jul. 5, 2024.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/446,654 mailed Jun. 25, 2024.
Non-Final Office Action for U.S. Appl. No. 17/450,864 mailed May 29, 2024.

(56) References Cited

OTHER PUBLICATIONS

Non-Final Office Action for U.S. Appl. No. 17/451,345 mailed Jul. 25, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/646,771 mailed Apr. 24, 2024.
Non-Final Office Action for U.S. Appl. No. 17/653,314 mailed Aug. 29, 2024.
Non-Final Office Action for U.S. Appl. No. 17/653,920 mailed Mar. 15, 2024.
Non-Final Office Action for U.S. Appl. No. 17/653,920 mailed Nov. 27, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/749,340 mailed Aug. 14, 2024.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/907,125 mailed Dec. 13, 2024.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/389,009 mailed May 24, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 16/478,180 mailed Dec. 16, 2024.
Notice of Allowance for U.S. Appl. No. 16/904,868 mailed Sep. 29, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/326,980 mailed Apr. 5, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/453,260 mailed Apr. 8, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/646,771 mailed Dec. 17, 2024.
Notice of Allowance for U.S. Appl. No. 17/657,474 mailed May 2, 2024.
Notice of Allowance for U.S. Appl. No. 17/661,090 mailed Oct. 30, 2024.
Notice of Allowance for U.S. Appl. No. 17/662,700 mailed Jun. 12, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Apr. 17, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/415,080 mailed Dec. 30, 2024.
Notice of Allowance for U.S. Appl. No. 18/426,795 mailed Nov. 20, 2024.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/878,268 mailed Sep. 20, 2024.
Restriction Requirement for U.S. Appl. No. 17/809,083 mailed Dec. 31, 2024.
U.S. Appl. No. 17/013,822, filed Sep. 7, 2020.
U.S. Appl. No. 18/662,216, filed May 13, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.

(56) References Cited

OTHER PUBLICATIONS

U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 63/564,696, filed Mar. 13, 2024.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
"OBLONG", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Wikipedia Article, "Decibel", https://web.archive.org/web/20200415121917/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
"Foam Packaging Isnert: Best Selection Guide" https://web/archive.org/web/20170922162235/http://www.foamtechchina/com:80/foam-packaging-insert/, Sep. 22, 2017, 25 pages.
"Surface Energy Data for Cellulose acetate, CAS # 9004-35-7" Diversified Enterprises, 2009, 1 page.
Advisory Action for U.S. Appl. No. 16/452,258 mailed May 5, 2025.
Advisory Action for U.S. Appl. No. 17/446,654 mailed Feb. 28, 2025.
Advisory Action for U.S. Appl. No. 17/451,345 mailed May 13, 2025.
Advisory Action for U.S. Appl. No. 17/595,747 mailed Mar. 17, 2025.
Advisory Action for U.S. Appl. No. 17/597,673 mailed Jan. 7, 2025.
Advisory Action for U.S. Appl. No. 17/653,314 mailed Apr. 8, 2025.
Advisory Action for U.S. Appl. No. 17/655,464 mailed Feb. 25, 2025.
Advisory Action for U.S. Appl. No. 17/664,487 mailed Apr. 24, 2025.
Advisory Action for U.S. Appl. No. 17/757,311 mailed Jul. 2, 2025.
Advisory Action for U.S. Appl. No. 18/003,029 mailed Jan. 8, 2025.
Advisory Action for U.S. Appl. No. 18/164,800 mailed Jan. 8, 2025.
Corrected Notice of Allowability for U.S. Appl. No. 17/646,771 mailed Jan. 17, 2025.
Corrected Notice of Allowability for U.S. Appl. No. 17/996,253 mailed Apr. 28, 2025.
Corrected Notice of Allowability for U.S. Appl. No. 18/134,857 mailed Mar. 14, 2025.
Corrected Notice of Allowance for U.S. Appl. No. 17/444,792 mailed Jun. 24, 2025.
Final Office Action for U.S. Appl. No. 16/452,258 mailed Jan. 6, 2025.
Final Office Action for U.S. Appl. No. 17/378,015 mailed Jun. 18, 2025.
Final Office Action for U.S. Appl. No. 17/446,256 mailed Jun. 11, 2025.
Final Office Action for U.S. Appl. No. 17/451,345 mailed Feb. 6, 2025.
Final Office Action for U.S. Appl. No. 17/597,408 mailed Mar. 24, 2025.
Final Office Action for U.S. Appl. No. 17/614,173 mailed May 20, 2025.
Final Office Action for U.S. Appl. No. 17/625,941 mailed Feb. 18, 2025.
Final Office Action for U.S. Appl. No. 17/628,411 mailed Apr. 30, 2025.
Final Office Action for U.S. Appl. No. 17/653,137 mailed Jun. 25, 2025.
Final Office Action for U.S. Appl. No. 17/653,314 mailed Jan. 30, 2025.
Final Office Action for U.S. Appl. No. 17/653,920 mailed Apr. 24, 2025.
Final Office Action for U.S. Appl. No. 17/664,487 mailed Jan. 13, 2025.
Final Office Action for U.S. Appl. No. 17/757,311 mailed Mar. 31, 2025.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/907,125 mailed Apr. 30, 2025.
Final Office Action for U.S. Appl. No. 18/139,523 mailed May 8, 2025.
International Search Report and Written Opinion from International Application No. PCT/US2023/031432 mailed Feb. 29, 2024.
International Search Report and Written Opinion from International Application No. PCT/US2023/036875 mailed May 31, 2024.
International Search Report and Written Opinion from International Application No. PCT/US2023/077205 mailed Jul. 19, 2024.
International Search Report and Written Opinion from International Application No. PCT/US2024/053681 mailed Jan. 27, 2025.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
International Search Report and Written Opinion from International Application No. PCT/US2025/018913 mailed Jun. 18, 2025.
Issue Notification for U.S. Appl. No. 16/478,180 mailed Mar. 5, 2025.
Issue Notification for U.S. Appl. No. 16/904,868 mailed Apr. 30, 2025.
Issue Notification for U.S. Appl. No. 17/051,585 mailed Mar. 26, 2025.
Issue Notification for U.S. Appl. No. 17/444,792 mailed Jun. 25, 2025.
Issue Notification for U.S. Appl. No. 17/450,864 mailed Jan. 8, 2025.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/597,673 mailed Jun. 4, 2025.
Issue Notification for U.S. Appl. No. 17/646,771 mailed Mar. 19, 2025.
Issue Notification for U.S. Appl. No. 17/661,090 mailed Feb. 5, 2025.
Issue Notification for U.S. Appl. No. 17/663,330 mailed Feb. 26, 2025.
Issue Notification for U.S. Appl. No. 17/749,340 mailed May 28, 2025.
Issue Notification for U.S. Appl. No. 17/758,316 mailed Jun. 25, 2025.
Issue Notification for U.S. Appl. No. 18/134,857 mailed May 28, 2025.
Issue Notification for U.S. Appl. No. 18/140,751 mailed Feb. 12, 2025.

(56) References Cited

OTHER PUBLICATIONS

Issue Notification for U.S. Appl. No. 18/415,080 mailed Apr. 9, 2025.
Issue Notification for U.S. Appl. No. 18/426,795 mailed Feb. 19, 2025.
Issue Notification for U.S. Appl. No. 18/584,002 mailed Apr. 16, 2025.
Non-Final Office Action for U.S. Appl. No. 16/433,773 mailed Feb. 28, 2025.
Non-Final Office Action for U.S. Appl. No. 17/051,600 mailed Feb. 28, 2025.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/446,654 mailed May 1, 2025.
Non-Final Office Action for U.S. Appl. No. 17/451,354 mailed Mar. 19, 2025.
Non-Final Office Action for U.S. Appl. No. 17/595,747 mailed Jun. 12, 2025.
Non-Final Office Action for U.S. Appl. No. 17/631,619 mailed Mar. 19, 2025.
Non-Final Office Action for U.S. Appl. No. 17/645,821 mailed Mar. 31, 2025.
Non-Final Office Action for U.S. Appl. No. 17/653,137 mailed Jan. 28, 2025.
Non-Final Office Action for U.S. Appl. No. 17/653,314 mailed May 8, 2025.
Non-Final Office Action for U.S. Appl. No. 17/655,464 mailed Mar. 20, 2025.
Non-Final Office Action for U.S. Appl. No. 17/664,487 mailed May 19, 2025.
Non-Final Office Action for U.S. Appl. No. 17/754,736 mailed Mar. 31, 2025.
Non-Final Office Action for U.S. Appl. No. 17/756,201 mailed Apr. 24, 2025.
Non-Final Office Action for U.S. Appl. No. 17/809,083 mailed Apr. 2, 2025.
Non-Final Office Action for U.S. Appl. No. 17/809,083 mailed Mar. 7, 2025.
Non-Final Office Action for U.S. Appl. No. 17/878,268 mailed Mar. 17, 2025.
Non-Final Office Action for U.S. Appl. No. 17/912,147 mailed May 29, 2025.
Non-Final Office Action for U.S. Appl. No. 17/929,887 mailed Jun. 25, 2025.
Non-Final Office Action for U.S. Appl. No. 17/930,238 mailed Jun. 30, 2025.
Non-Final Office Action for U.S. Appl. No. 17/996,064 mailed Mar. 6, 2025.
Non-Final Office Action for U.S. Appl. No. 18/003,029 mailed Apr. 18, 2025.
Non-Final Office Action for U.S. Appl. No. 18/006,807 mailed May 29, 2025.
Non-Final Office Action for U.S. Appl. No. 18/042,842 mailed May 22, 2025.
Non-Final Office Action for U.S. Appl. No. 18/043,618 mailed May 19, 2025.
Non-Final Office Action for U.S. Appl. No. 18/164,800 mailed Apr. 25, 2025.
Non-Final Office Action for U.S. Appl. No. 18/247,986 mailed Jun. 4, 2025.
Non-Final Office Action for U.S. Appl. No. 18/264,004 mailed May 15, 2025.
Non-Final Office Action for U.S. Appl. No. 18/265,736 mailed Jul. 1, 2025.
Notice of Allowance for U.S. Appl. No. 16/904,868 mailed Jan. 21, 2025.
Notice of Allowance for U.S. Appl. No. 17/444,792 mailed Mar. 28, 2025.
Notice of Allowance for U.S. Appl. No. 17/451,345 mailed Jun. 24, 2025.
Notice of Allowance for U.S. Appl. No. 17/596,629 mailed Jan. 29, 2025.
Notice of Allowance for U.S. Appl. No. 17/596,629 mailed May 27, 2025.
Notice of Allowance for U.S. Appl. No. 17/597,673 mailed Feb. 26, 2025.
Notice of Allowance for U.S. Appl. No. 17/653,920 mailed Jul. 9, 2025.
Notice of Allowance for U.S. Appl. No. 17/749,340 mailed Feb. 14, 2025.
Notice of Allowance for U.S. Appl. No. 17/758,316 mailed Mar. 24, 2025.
Notice of Allowance for U.S. Appl. No. 17/996,155 mailed Jun. 24, 2025.
Notice of Allowance for U.S. Appl. No. 17/996,155 mailed Mar. 11, 2025.
Notice of Allowance for U.S. Appl. No. 17/996,253 mailed Apr. 11, 2025.
Notice of Allowance for U.S. Appl. No. 17/996,468 mailed Apr. 14, 2025.
Notice of Allowance for U.S. Appl. No. 18/007,105 mailed Jun. 17, 2025.
Notice of Allowance for U.S. Appl. No. 18/134,857 mailed Feb. 20, 2025.
Notice of Allowance for U.S. Appl. No. 18/584,002 mailed Jan. 8, 2025.
Restriction Requirement for U.S. Appl. No. 17/755,236 mailed Apr. 24, 2025.
Restriction Requirement for U.S. Appl. No. 17/929,887 mailed Mar. 10, 2025.
Restriction Requirement for U.S. Appl. No. 17/930,238 mailed Apr. 17, 2025.
Restriction Requirement for U.S. Appl. No. 18/041,109 mailed Jun. 4, 2025.
Restriction Requirement for U.S. Appl. No. 18/150,360 mailed May 19, 2025.
Supplemental Notice of Allowance for U.S. Appl. No. 17/597,673 mailed Apr. 10, 2025.
U.S. Appl. No. 17/596,629, filed Dec. 15, 2021.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/103,165, filed Feb. 11, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 63/181,709, filed Apr. 29, 2021.
"TUBE Definition & Meaning" Merriam Webster Dictionary, 2025, <https://www.merriam-webster.com/dictionary/tube>.
Advisory Action for U.S. Appl. No. 17/378,015 mailed Oct. 28, 2025.
Advisory Action for U.S. Appl. No. 17/446,256 mailed Nov. 6, 2025.

(56) References Cited

OTHER PUBLICATIONS

Corrected Notice of Allowability for U.S. Appl. No. 17/653,314 mailed Oct. 29, 2025.
Corrected Notice of Allowability for U.S. Appl. No. 17/808,354 mailed Nov. 25, 2025.
Corrected Notice of Allowability for U.S. Appl. No. 18/260,122 mailed Aug. 11, 2025.
Di Mauro, et al., "Penile length and circumference dimensions: A large study in young Italian men" Reconstructive Urology, Men's Health Working Parties of the European Association of Urology (EAU) Young Academic Urologists (YAU). pp. 1-7, Mar. 8, 2021.
Final Office Action for U.S. Appl. No. 17/051,600 mailed Aug. 6, 2025.
Final Office Action for U.S. Appl. No. 17/394,055 mailed Sep. 24, 2025.
Final Office Action for U.S. Appl. No. 17/631,619 mailed Oct. 1, 2025.
Final Office Action for U.S. Appl. No. 18/003,029 mailed Nov. 26, 2025.
Final Office Action for U.S. Appl. No. 18/043,618 mailed Nov. 26, 2025.
Final Office Action for U.S. Appl. No. 18/164,800 mailed Dec. 5, 2025.
Final Office Action for U.S. Appl. No. 18/265,736 mailed Dec. 1, 2025.
Issue Notification for U.S. Appl. No. 17/653,920 mailed Oct. 22, 2025.
Issue Notification for U.S. Appl. No. 17/755,236 mailed Oct. 29, 2025.
Issue Notification for U.S. Appl. No. 17/996,064 mailed Nov. 5, 2025.
Issue Notification for U.S. Appl. No. 17/996,155 mailed Oct. 8, 2025.
Issue Notification for U.S. Appl. No. 17/996,253 mailed Oct. 29, 2025.
Issue Notification for U.S. Appl. No. 17/996,468 mailed Nov. 26, 2025.
Issue Notification for U.S. Appl. No. 18/007,105 mailed Oct. 1, 2025.
Issue Notification for U.S. Appl. No. 18/260,122 mailed Nov. 12, 2025.
Non-Final Office Action for U.S. Appl. No. 16/452,258 mailed Sep. 24, 2025.
Non-Final Office Action for U.S. Appl. No. 17/378,015 mailed Dec. 12, 2025.
Non-Final Office Action for U.S. Appl. No. 17/446,256 mailed Dec. 2, 2025.
Non-Final Office Action for U.S. Appl. No. 17/635,866 mailed Jul. 29, 2025.
Non-Final Office Action for U.S. Appl. No. 17/759,697 mailed Sep. 17, 2025.
Non-Final Office Action for U.S. Appl. No. 17/933,590 mailed Jul. 29, 2025.
Non-Final Office Action for U.S. Appl. No. 18/115,444 mailed Oct. 22, 2025.
Non-Final Office Action for U.S. Appl. No. 18/139,523 mailed Nov. 19, 2025.
Non-Final Office Action for U.S. Appl. No. 18/150,360 mailed Nov. 5, 2025.
Non-Final Office Action for U.S. Appl. No. 18/249,577 mailed Nov. 17, 2025.
Non-Final Office Action for U.S. Appl. No. 18/254,638 mailed Nov. 17, 2025.
Non-Final Office Action for U.S. Appl. No. 18/259,626 mailed Jul. 11, 2025.
Non-Final Office Action for U.S. Appl. No. 18/264,278 mailed Nov. 10, 2025.
Non-Final Office Action for U.S. Appl. No. 18/548,152 mailed Sep. 16, 2025.
Non-Final Office Action for U.S. Appl. No. 18/553,625 mailed Oct. 2, 2025.
Non-Final Office Action for U.S. Appl. No. 18/757,964 mailed Aug. 20, 2025.
Notice of Allowance for U.S. Appl. No. 16/433,773 mailed Oct. 10, 2025.
Notice of Allowance for U.S. Appl. No. 17/051,399 mailed Nov. 17, 2025.
Notice of Allowance for U.S. Appl. No. 17/451,354 mailed Nov. 18, 2025.
Notice of Allowance for U.S. Appl. No. 17/625,941 mailed Nov. 13, 2025.
Notice of Allowance for U.S. Appl. No. 17/645,821 mailed Nov. 24, 2025.
Notice of Allowance for U.S. Appl. No. 17/653,137 mailed Oct. 22, 2025.
Notice of Allowance for U.S. Appl. No. 17/653,314 mailed Oct. 20, 2025.
Notice of Allowance for U.S. Appl. No. 17/755,236 mailed Jul. 17, 2025.
Notice of Allowance for U.S. Appl. No. 17/808,354 mailed Nov. 12, 2025.
Notice of Allowance for U.S. Appl. No. 17/878,268 mailed Oct. 15, 2025.
Notice of Allowance for U.S. Appl. No. 17/907,125 mailed Sep. 26, 2025.
Notice of Allowance for U.S. Appl. No. 17/912,147 mailed Dec. 3, 2025.
Notice of Allowance for U.S. Appl. No. 17/930,238 mailed Dec. 16, 2025.
Notice of Allowance for U.S. Appl. No. 17/996,064 mailed Jul. 29, 2025.
Notice of Allowance for U.S. Appl. No. 17/996,253 mailed Jul. 11, 2025.
Notice of Allowance for U.S. Appl. No. 17/996,468 mailed Jul. 15, 2025.
Notice of Allowance for U.S. Appl. No. 18/044,413 mailed Sep. 16, 2025.
Notice of Allowance for U.S. Appl. No. 18/260,122 mailed Jul. 30, 2025.
Restriction Requirement for U.S. Appl. No. 17/625,887 mailed Sep. 2, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Oct. 23, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/294,370 mailed Nov. 26, 2025.
Restriction Requirement for U.S. Appl. No. 18/373,424 mailed Nov. 14, 2025.
Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/551,492 mailed Nov. 10, 2025.
Restriction Requirement for U.S. Appl. No. 18/662,216 mailed Nov. 26, 2025.
Restriction Requirement for U.S. Appl. No. 19/237,638 mailed Dec. 18, 2025.
U.S. Appl. No. 18/034,902, filed May 2, 2023.
U.S. Appl. No. 19/329,723, filed Sep. 16, 2025.
U.S. Appl. No. 19/337,217, filed Sep. 23, 2025.
U.S. Appl. No. 19/356,506, filed Oct. 13, 2025.
U.S. Appl. No. 19/358,647, filed Oct. 15, 2025.

(56) References Cited

OTHER PUBLICATIONS

U.S. Appl. No. 19/370,361, filed Oct. 27, 2025.
U.S. Appl. No. 19/418,150, filed Dec. 12, 2025.
U.S. Appl. No. 19/491,481, filed Dec. 9, 2025.
U.S. Appl. No. 19/494,631, filed Dec. 18, 2025.

* cited by examiner

URINE COLLECTION SYSTEM INCLUDING A SIZING DEVICE

CROSS-REFERENCE TO RELATED APPLICATIONS

This application is a U.S. Nationalization of PCT International Application No. PCT/US2020/067451 filed on 30 Dec. 2020, which claims priority to U.S. Provisional Patent Application No. 62/956,767 filed on Jan. 3, 2020, the disclosure of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experienced by pilots, drivers, and workers in hazardous areas. Additionally, fluid collection from the individual may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

Thus, users and manufacturers of urine collection devices continue to seek new and improved devices, systems, and methods to collect urine.

SUMMARY

Embodiments disclosed herein are related to urine collection devices and methods of using urine collection devices. In an embodiment, a sizing device for a urine collection system includes a body and a recess. The body has a distal end and an attachment end spaced from the distal end, with the attachment end defining an opening. The recess extends into the body from the opening, with the recess sized and dimensioned to receive a portion of a urine collection device and secure the sizing device to the urine collection device.

In an embodiment, a urine collection system includes a urine collection device and a sizing device. The sizing device is secured or securable to the urine collection device and includes a body and a recess. The body has a distal end and an attachment end spaced from the distal end, with the attachment end defining an opening. The recess extends into the body from the opening, with the recess being sized and dimensioned to receive a portion of the urine collection device and secure the sizing device to the urine collection device.

In an embodiment a method of positioning a urine collection system on an individual or patient is disclosed. The method includes positioning a urine collection device between legs of the individual. The method also includes determining whether securing a sizing device to the urine collection device will improve securement of the urine collection device between the legs of the individual. The method also includes securing the sizing device to a distal portion of the urine collection device. The method also includes positioning the urine collection device with the sizing device secured thereto between the legs of the individual.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are related to urine collection systems and methods of using the same. The urine collection devices and systems disclosed herein are configured to collect fluids from an individual. The fluids collected by the urine collection devices may include at least one of urine, vaginal discharge, penile discharge, reproductive fluids, blood, sweat, or other bodily fluids. The urine collection systems can include a urine collection device, a sizing device, a fluid storage container, and a portable vacuum source. The sizing device may be used to more securely position the urine collection device between the legs of an individual using the fluid collection device.

Conventional urine collection devices typically have a size and shape that cannot by modified. Thus, while patients using the urine collection devices have physical or anatomical features that differ in size, geometry, etc., from one patient to another, conventional urine collection devices are not configured to adapt in size and geometry for the varying size and geometry of the physical features of individual patients. This lack of adaptability of the urine collection devices may result in urine collection devices that do not efficiently secure in the desired position between the legs of the user. For example, in a significantly underweight patient, the gap between the legs may be significantly wider than a width of a conventional urine collection device, leaving the conventional urine collection device with a high degree of mobility between the legs and increasing the likelihood of the urine collection device moving from the desired position. In another example, a conventional urine collection device may not be long enough to have a portion of the urine collection device secured at least partially between the buttocks of the patient.

To improve securement of a urine collection device between the legs of a patient using the urine collection device, embodiments of urine collections systems described herein includes a sizing device. As shall be described in greater detail below, the sizing device may provide an increased width, length, or both width and length to improve securement of the urine collection device in a desired positioned between the legs of the patient using the urine collection device. The sizing device may be removably secured to the urine collection device. For example, the sizing device may include a body and a recess in the body that is sized and shaped complementary to a distal portion of the urine collection device to allow a distal portion of the urine collection device to be secured within the recess on the urine collection device. The sizing device may include one or more of a substantially conical shape, a wedge shape, a bulbous shape, a disc shape, or other suitable shapes. The sizing devices described herein may be detached from the urine collection device after use, thereby allowing the sizing device to be cleaned and reused.

Figure 1:
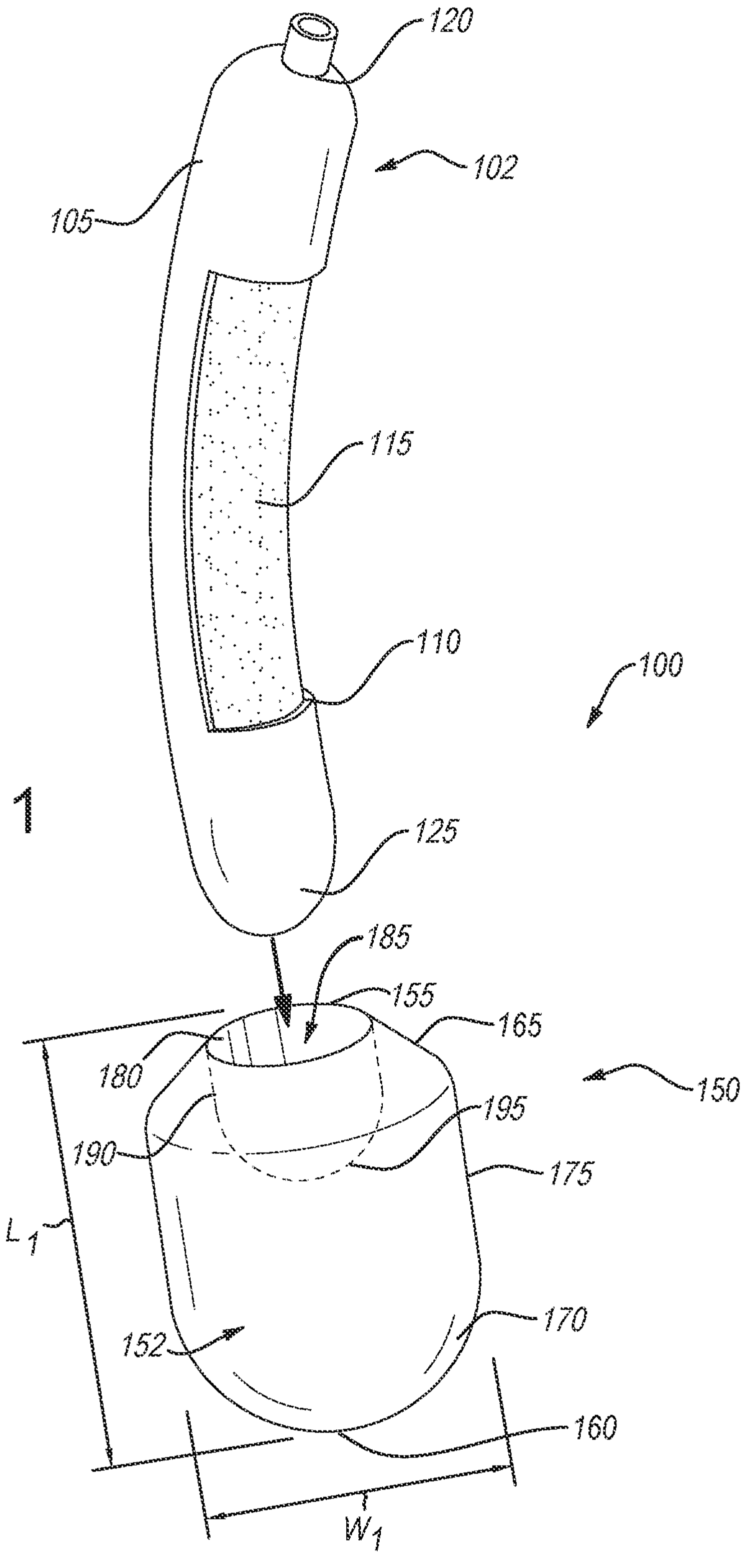
FIG. 1 is an isometric view of a urine collection system including a sizing device, according to an embodiment.

FIG. 1 is an isometric view of a urine collection device 102 and a sizing device 150 of a urine collection system 100. Although not shown in FIG. 1, the urine collection system 100 also may include a fluid storage container and a portable vacuum source, as described below in the block diagram of FIG. 4. The urine collection device 102 may include a fluid impermeable barrier 105 having an end portion 125 and at least partially defining a chamber, an aperture 120 distal to the end portion 125 and configured to receive a conduit therethrough, and an opening 110 between the aperture 120 and the end portion 125. A fluid permeable support 115 may be positioned at least partially within the chamber defined by the fluid impermeable barrier 105 to extend across at least a portion of the opening 110. The fluid permeable support 115 may be configured to wick fluid from the opening 110 into the chamber for removal from the urine collection device. The fluid permeable support 115 includes an outer layer of a fluid permeable membrane including gauze and an inner support of a porous nylon structure.

The fluid impermeable barrier 105 may be generally tubular or cylindrical. Accordingly, the end portion 125 of the fluid impermeable barrier 105 may be generally tubular. For example, in the urine collection device 102 shown in FIG. 1, the end portion 125 is a tapered end portion having a cylindrical portion a rounded or semispherical portion. While the end portion 125 forms a portion of the fluid impermeable barrier 105 of the urine collection device 102, in other embodiments, the end portion 125 may be secured to the fluid impermeable barrier 105 and may include a different material than the fluid impermeable barrier 105. Other embodiments of urine collection devices including fluid impermeable barriers, fluid permeable supports, chambers, and their shapes and configurations are disclosed in U.S. patent application Ser. No. 15/260,103 filed on Sep. 8, 2016 and U.S. patent application Ser. No. 15/611,587 filed on Jun. 1, 2017, the disclosure of each of which is incorporated herein, in its entirety, by this reference.

The sizing device 150 is configured to be detachably secured to the urine collection device 102 at the end portion 125 of the urine collection device 102. The sizing device 150 may be secured to the urine collection device 102 for use with a patient, then removed from the urine collection device 102, cleaned, and reused on a different urine collection device 102 and/or with a different patient. The sizing device 150 is sized and dimensioned to provide both additional length and width to the urine collection device 102.

The sizing device 150 includes a body 152 and a recess 185. The body 152 may be formed from a biocompatible material that will not cause excess friction, harm, or discomfort to the patient using the urine collection device 102 and the sizing device 150. For example, the body 152 may include one or more of a biocompatible foam, silicone, latex rubber, or other suitable material. In some embodiments, the body 152 includes substantially the same material as the fluid impermeable membrane 105 of the urine collection device 105. The body 152 of the sizing device 150 may be substantially hollow and filled with air. In some embodiments, the body 152 may be filled with a relatively soft or pliable material, or may be filled with the same biocompatible material forming the outer surface of the body 152.

The body 152 of the sizing device 150 includes a head 165, a base 170, an attachment end 155 at the head 165, an opening 180 defined by the attachment end 155 and/or the head 165, and a distal end 160 at the base 170. The head 165 may be substantially frustoconical and taper to the attachment end 155, and the base 170 may be substantially semispherical and taper to the distal end 160 of the body 152. The body 152 also may include a substantially cylindrical portion 175 between the head 165 and the base 170. In some embodiments, the head 165 tapers from the cylindrical portion 175 to the opening 180 at the attachment end 155 to form the substantially frustoconical shape of the head 165. The head 165 may taper continuously or only partially between the cylindrical portion 175 and the attachment end 155. In some embodiments, the base 170 tapers from the cylindrical portion 175 to the distal end 160 to form the substantially semispherical shape of the base 170. The base 170 may taper continuously or only partially between the cylindrical portion 175 and the distal end 160.

The body 152 includes a length $L_1$ from the attachment end 155 to the distal end 160. The length $L_1$ may vary according to different embodiments. For example, the length $L_1$ may be at least about 2.5 cm, at least about 3.8 cm, at least about 5.1 cm, at least about 6.4 cm, at least about 7.6 cm, at least about 8.9 cm, at least about 10.2 cm, about 2.5 cm to about 12.7 cm, about 2.5 cm to about 7.6 cm, about 7.6 cm to about 12.7 cm, about 2.5 cm to about 5.1 cm, about 5.1 cm to about 7.6 cm, about 7.6 cm to about 10.2 cm, about 10.2 cm to about 12.7 cm, about 2.5 cm, about 3.8 cm, about 5.1 cm, about 6.4 cm, about 7.6 cm, about 8.9 cm, or about 10.2 cm.

The body 152 also includes a maximum width $W_1$ that may, for example, be the diameter of the cylindrical portion 175. The maximum width $W_1$ may vary according to different embodiments. For example, the maximum width $W_1$ may be at least about 3.8 cm, at least about 5.1 cm, at least about 6.4 cm, at least about 7.6 cm, at least about 8.9 cm, at least about 10.2 cm, about 2.5 cm to about 12.7 cm, about 3.8 cm to about 7.6 cm, about 7.6 cm to about 12.7 cm, about 3.8 cm to about 5.1 cm, about 5.1 cm to about 7.6 cm, about 7.6 cm to about 10.2 cm, about 10.2 cm to about 12.7 cm, about 3.8 cm, about 5.1 cm, about 6.4 cm, about 7.6 cm, about 8.9 cm, or about 10.2 cm.

The opening 180 may include a width substantially equal to a width of the end portion 125 of the urine collection device 102, such as a diameter of the cylindrical portion of the end portion 125. For example, the opening may include a width or diameter of about 1.3 cm to about 5.1 cm, about 1.3 cm to about 2.5 cm, about 2.5 cm to about 3.8 cm, about 3.8 cm to about 5.1 cm, about 1.3 cm, about 1.9 cm, about 2.5 cm, about 3.2 cm, about 3.8 cm, about 4.4 cm, or about 5.1 cm.

The sizing device 150 also includes the recess 185 extending partially into the body 152 from the opening 180. In the sizing device 150 shown in FIG. 1, the recess 185 extends partially into the body 152 from the opening 180 at the distal end 155 of the body 152. In other embodiments, however, the opening 180 and recess 185 may be positioned elsewhere on the body 152, such as a sloped wall of the head 165 or the cylindrical portion 175. The recess 185 may be defined at least partially by an inner surface of the head 165. In some embodiments, the recess 185 is defined at least partially by an inner surface of the head 165 and an inner surface of the cylindrical portion 175. The inner surface(s) defining the recess 185 may include any of the materials described above in relation to the material of the body 152. The inner surface(s) defining the recess 185 additionally or alternatively may include one or more of a hook or loop material (such as VELCRO®), an adhesive, or tape.

The recess 185 may be shaped complementary to the end portion 125 of the urine collection device 102. For example, the recess 185 may include a cylindrical portion 190 and a semispherical portion 195 shaped to correspond with part of the cylindrical portion and the semispherical portion of the end portion 125 of the urine collection device 102. The recess 185 may include a maximum width or diameter substantially equal to any of the width described above in relation to the opening 180. The recess 185 also includes a maximum depth from the opening 180 to the bottom of the recess 185. The depth may be about 0.64 cm to about 3.8 cm, about 0.64 cm to about 1.3 cm, about 1.3 cm to about 1.9 cm, about 1.9 cm to about 2.5 cm, about 2.5 cm to about 3.2 cm, about 3.2 cm to about 3.8 cm, at least about 0.64 cm, at least about 1.3 cm, at least about 1.9 cm, at least about 2.5 cm, at least about 3.2 cm, or at least about 3.8 cm. In some embodiments, the recess 185 includes a through hole that passes through the body 152, the through hole being sized to allow at least a portion of the urine collection device 102 to slide through the through hole and protrude from the distal end 160 of the body 152.

The end portion 125 of the urine collection device 102 may be secured within the recess 185 due to one or more of friction from tight tolerances between the end portion 125 and the inner surface(s) defining the recess 185, an elastic material in at least one of the end portion 125 or the inner surface(s) defining recess 185, an interlock system between the end portion 125 and body 152, a hook and loop system (such as VELCRO®), one or more adhesives, tape, clips, or other suitable materials. In use, the end portion 125 of the urine collection device 102 may be inserted into the recess 185 of the sizing device 150 to secure the sizing device 150 to the urine collection device 102. Securing the sizing device 150 to the urine collection device 102 adds increased length and width to the urine collection device 102. With additional length and width added to urine collection device 102, stability and securement of the urine collection device 102 between the legs of the patient using the urine collection device 102 may be improved.

Figure 2:
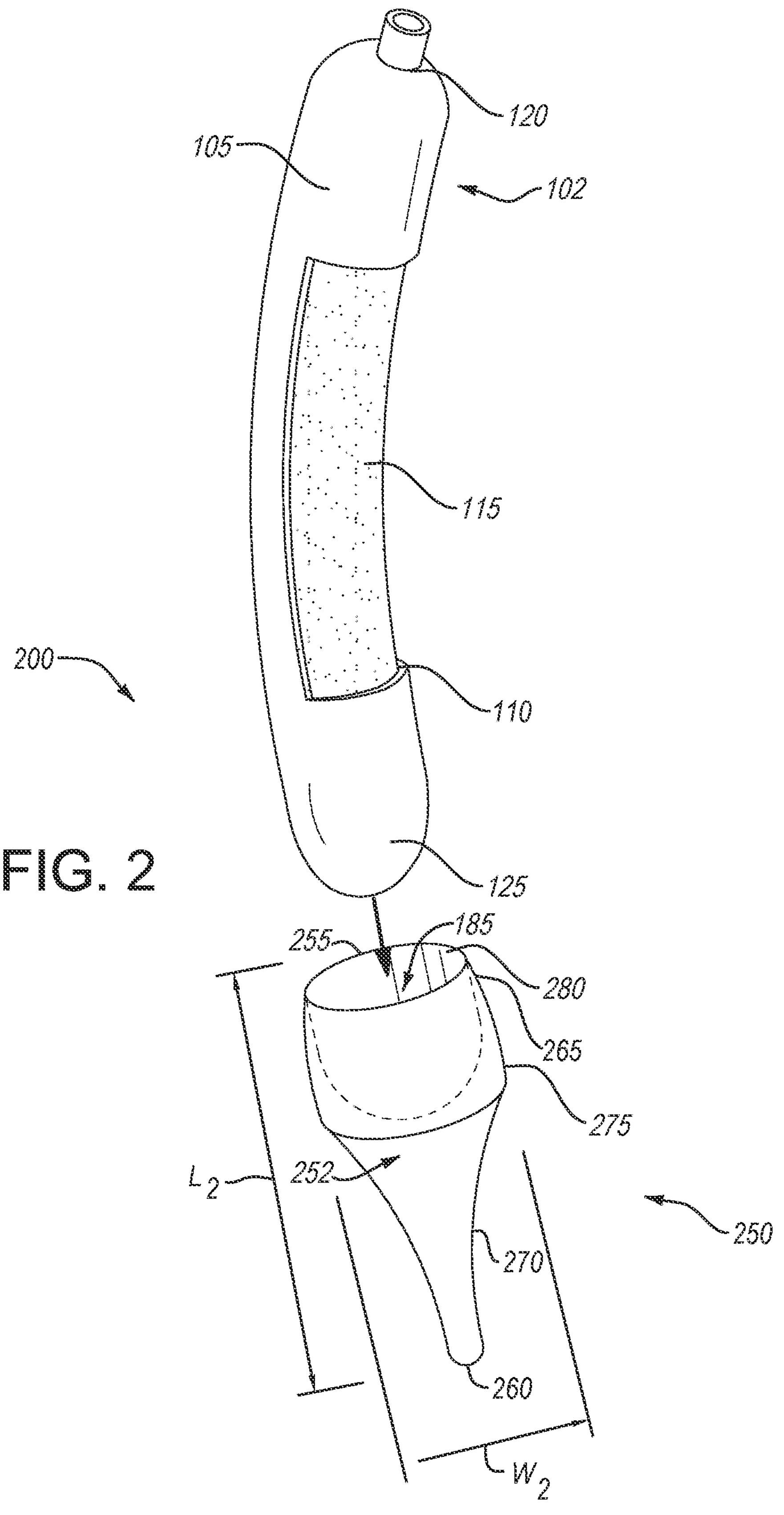
FIG. 2 is an isometric view of a urine collection system including a sizing device, according to an embodiment.

FIG. 2 is an isometric view of the urine collection device 102 and a sizing device 250 of a urine collection system 200. Although not shown in FIG. 2, the urine collection system 200 also may include a fluid storage container and a portable vacuum source, as described above. The sizing device 250 is configured to detachably secure to the urine collection device 102 at the end portion 125 of the urine collection device 102. The sizing device 250 may be secured to the urine collection device 102 for use with a patient, then removed from the urine collection device 102, cleaned, and reused on a different urine collection device 102 and/or with a different patient. The sizing device 250 is sized and dimensioned to provide at least additional length to the urine collection device 102.

The sizing device 250 includes a body 252 and the recess 185. The recess 185 may include any of the features, dimensions, and characteristics described above in relation to the sizing device 150. The body 252 may be formed from any of the materials described above in relation to the body 152 of the sizing device 150.

The body 252 of the sizing device 250 includes a head 265, a base 270, an attachment end 255 at the head 265, an opening 280 defined by the attachment end 255 and/or the head 265, and a distal end 260 at the base 270. The head 265 may be at least partially frustoconical and taper to the attachment end 255, and the base 270 may be an elongated conical or frustoconical shape that tapers to the distal end 260 of the body 252. More particularly, the base 270 may have generally inward curved or concave sides as the base tapers to the distal end 260. The body 252 also may include a substantially cylindrical portion 275 between the head 265 and the base 270. In some embodiments, the head 265 tapers from the cylindrical portion 275 to the opening 280 at the attachment end 255 to form the at least partially frustoconical shape of the head 265. The head 265 may taper continuously or only partially between the cylindrical portion 275 and the attachment end 255. In some embodiments, the base 270 tapers from the cylindrical portion 275 to the distal end 260 to form the elongated conical or frustoconical shape of the base 270. The base 270 may taper continuously or only partially between the cylindrical portion 275 and the distal end 260. In other embodiments, the body 252 includes a substantially cylindrical head 265 and the elongated conical or frustoconical base 270.

The body 252 includes a length $L_2$ from the attachment end 255 to the distal end 260. The length $L_2$ may vary according to different embodiments. For example, the length $L_2$ may be at least about 2.5 cm, at least about 3.8 cm, at least about 5.1 cm, at least about 6.4 cm, at least about 7.6 cm, at least about 8.9 cm, at least about 10.2 cm, at least about 11.4 cm, at least about 12.7 cm, about 2.5 cm to about 15.24 cm, about 2.5 cm to about 7.6 cm, about 7.6 cm to about 12.7 cm, about 2.5 cm to about 5.1 cm, about 5.1 cm to about 7.6 cm, about 7.6 cm to about 10.2 cm, about 10.2 cm to about 12.7 cm, about 12.7 cm to about 15.24 cm, about 2.5 cm, about 3.8 cm, about 5.1 cm, about 6.4 cm, about 7.6 cm, about 8.9 cm, about 10.2 cm, about 4.12.7 cm, about 12.7 cm, about 14 cm, or about 15.24 cm.

The body 252 also includes a maximum width $W_2$ that may, for example, be the diameter of the cylindrical portion 275. The maximum width $W_2$ may vary according to different embodiments. For example, the maximum width $W_2$ may be at least about 2.5 cm, at least about 3.2 cm, at least about 3.8 cm, at least about 4.4 cm, at least about 5.1 cm, about 2.5 cm to about 5.1 cm, about 2.5 cm to about 3.2 cm, about 3.2 cm to about 3.8 cm, about 3.8 cm to about 4.4 cm, about 4.4 cm to about 5.1 cm, about 2.5 cm, about 3.2 cm, about 3.8 cm, or about 5.1 cm.

The opening 280 may include a width substantially equal to a width of the end portion 125 of the urine collection device 102, such as a diameter of the cylindrical portion of the end portion 125. For example, the opening 280 may include a width or diameter of about 1.3 cm to about 5.1 cm, about 1.3 cm to about 2.5 cm, about 2.5 cm to about 3.8 cm, about 3.8 cm to about 5.1 cm, about 1.3 cm, about 1.9 cm, about 2.5 cm, about 3.2 cm, about 3.8 cm, about 4.4 cm, or about 5.1 cm.

In use, the end portion 125 of the urine collection device 102 may be inserted into the recess 185 of the sizing device 250 to secure the sizing device 250 to the urine collection device 102. Securing the sizing device 250 to the urine collection device 102 adds increased length to the urine collection device 102. With additional length added to the urine collection device 102, stability and securement of the urine collection device 102 between the legs of the patient using the urine collection device 102 may be improved. For example, the length added to the urine collection device 102 may allow at least a portion of the base 270 to be positioned between the buttocks of the patient wearing the urine collection device 102.

Figure 3:
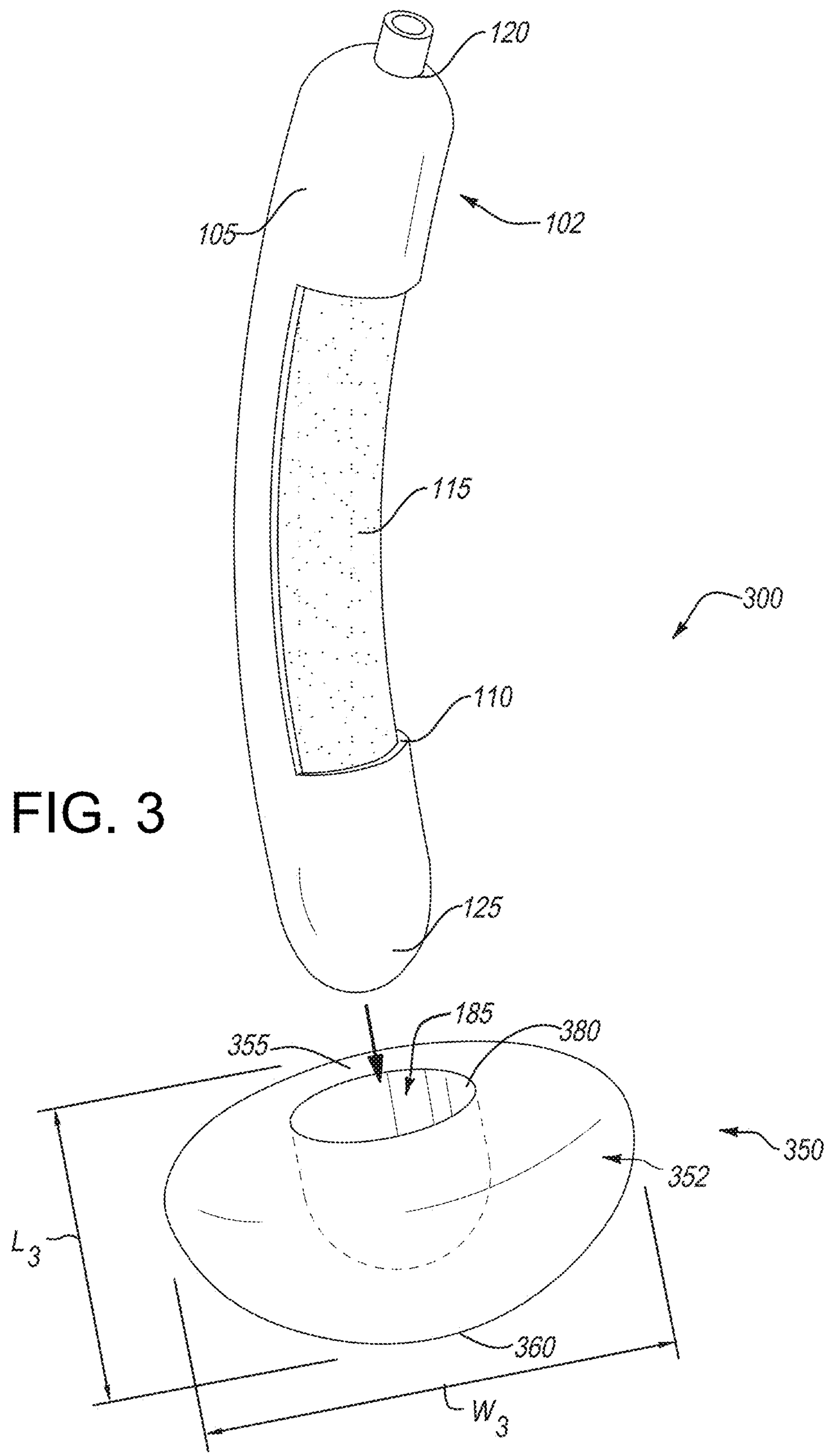
FIG. 3 is an isometric view of a urine collection system including a sizing device, according to an embodiment.

FIG. 3 is an isometric view of the urine collection device 102 and a sizing device 350 of a urine collection system 300. Although not shown in FIG. 3, the urine collection system 300 also may include a fluid storage container and a portable vacuum source, as described above. The sizing device 350 is configured to detachably secure to the urine collection device 102 at the end portion 125 of the urine collection device 102. The sizing device 350 may be secured to the urine collection device 102 for use with a patient, then removed from the urine collection device 102, cleaned, and reused on a different urine collection device 102 and/or with a different patient. The sizing device 350 is sized and dimensioned to provide at least additional width to the urine collection device 102.

The sizing device 350 includes a body 352 and the recess 185. The recess 185 may include any of the features, dimensions, and characteristics described above in relation to the sizing device 350. The body 352 may be formed from any of the materials described above in relation to the body 152 of the sizing device 150. The body 352 of the sizing device 350 includes an attachment end 355, an opening 380 defined by the attachment end, and a distal end 360 distal to the attachment end 355. The body 352 may be generally ellipsoidal, semispherical, spherical, or bulbous in shape.

The body 352 includes a length $L_3$ from the attachment end 355 to the distal end 360. The length $L_3$ may vary according to different embodiments. For example, the length $L_3$ may be at least about 2.5 cm, at least about 3.8 cm, at least about 5.1 cm, at least about 6.4 cm, at least about 7.6 cm, about 2.5 cm to about 10.2 cm, about 2.5 cm to about 7.6 cm, about 5.1 cm to about 10.2 cm, about 2.5 cm to about 5.1 cm, about 5.1 cm to about 7.6 cm, about 7.6 cm to about 10.2 cm, about 2.5 cm, about 3.8 cm, about 5.1 cm, about 6.4 cm, about 7.6 cm, about 8.9 cm, or about 10.2 cm.

The body 352 also includes a maximum width $W_3$ that may vary according to different embodiments. For example, the maximum width $W_3$ may be at least about 5.1 cm, at least about 6.4 cm, at least about 7.6 cm, at least about 8.9 cm, at least about 10.2 cm, about 5.1 cm to about 7.6 cm, about 7.6 cm to about 10.2 cm, about 10.2 cm to about 12.7 cm, about 5.1 cm, about 6.4 cm, about 7.6 cm, about 8.9 cm, or about 10.2 cm.

The opening 380 may include a width substantially equal to a width of the end portion 125 of the urine collection device 102, such as a diameter of the cylindrical portion of the end portion 125. For example, the opening 380 may include a width or diameter of about 1.3 cm to about 5.1 cm, about 1.3 cm to about 2.5 cm, about 2.5 cm to about 3.8 cm, about 3.8 cm to about 5.1 cm, about 1.3 cm, about 1.9 cm, about 2.5 cm, about 3.2 cm, about 3.8 cm, about 4.4 cm, or about 5.1 cm.

In use, the end portion 125 of the urine collection device 102 may be inserted into the recess 185 of the sizing device 350 to secure the sizing device 350 to the urine collection device 102. Securing the sizing device 350 to the urine collection device 102 adds increased width to the urine collection device 102. With additional width added to the urine collection device 102, stability and securement of the urine collection device 102 between the legs of the patient using the urine collection device 102 may be improved. For example, the width added to the urine collection device 102 may allow the sides of the sizing device 350 to contact the legs of the patient wearing the urine collection device 102.

Figure 4:
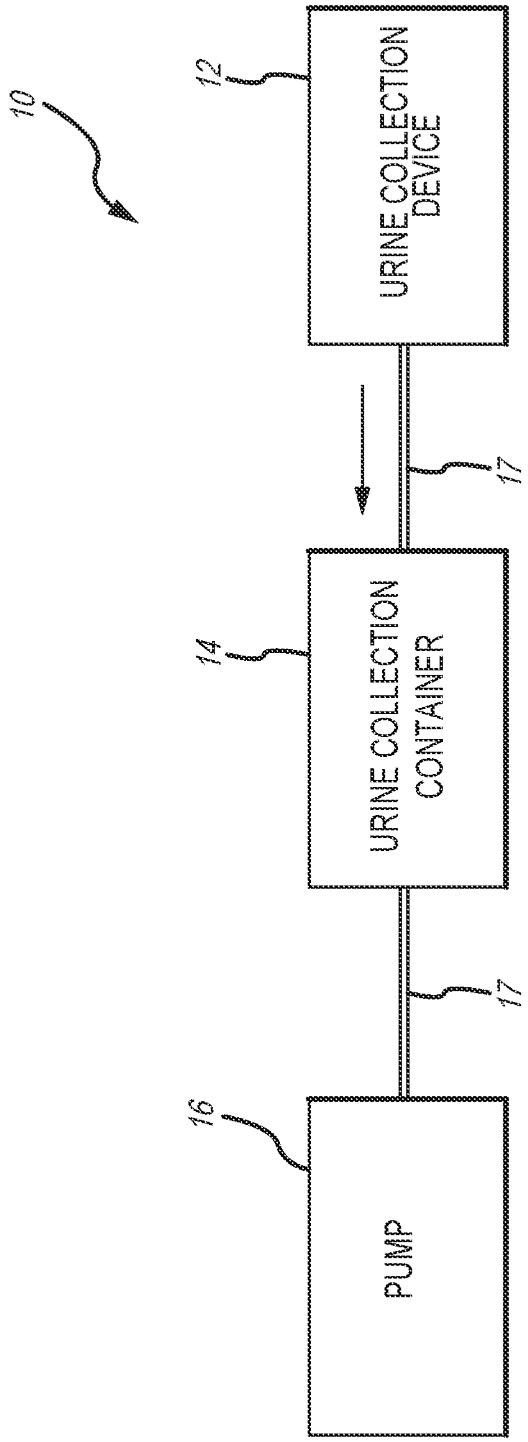
FIG. 4 is a block diagram of a urine collection system, according to an embodiment.

FIG. 4 is a block diagram of a fluid collection system 10, according to an embodiment. The fluid collection system 10 may be included in embodiments of fluid collection systems described herein. The system 10 includes a fluid (e.g., urine) collection device 12 (e.g., any of the fluid collection device disclosed herein), a urine collection container 14, and a pump 16 (or vacuum source). The fluid collection device 10, the urine collection container 14, and the pump 16 may be fluidly coupled to each other via one or more conduits 17. For example, fluid collection device 10 may be operably coupled to one or more of the urine collection container 14 or the pump 16 via the conduit 17. In some embodiments, the pump 16 may be secured directly to the urine collection container 14. Fluid (e.g., urine or other bodily fluids) collected in the fluid collection device 10 may be removed from the fluid collection device 10 via the conduit 17 secured to the fluid collection device 12. Suction force may be introduced into the chamber of the fluid collection device 12 via the inlet of the conduit 17 responsive to suction (e.g., vacuum) force applied at the outlet of the conduit 17.

The suction force may be applied to the outlet of the conduit 17 by the pump 16 either directly or indirectly. The suction force may be applied indirectly via the urine collection container 14. For example, the outlet of the conduit 17 may be disposed within or fluidly coupled to an interior region of the urine collection container 14 and an additional conduit 17 may extend from the urine collection container 14 to the pump 16. Accordingly, the pump 16 may apply suction to the fluid collection device 12 via the urine collection container 14. The suction force may be applied directly via the pump 16. For example, the outlet of the conduit 17 may be disposed within the pump 16. An additional conduit 17 may extend from the pump 16 to a point outside of the fluid collection device 12, such as to the urine collection container 14. In such examples, the pump 16 may be disposed between the fluid collection device 12 and the urine collection container 14.

The urine collection container 14 is sized and shaped to retain a fluid therein. The urine collection container 14 may include a bag (e.g., drainage bag), a bottle or cup (e.g., collection jar), or any other enclosed container for storing bodily fluid(s) such as urine. In some examples, the conduit 17 may extend from the fluid collection device 12 and attach to the urine collection container 14 at a first point therein. An additional conduit 17 may attach to the urine collection container 14 at a second point thereon and may extend and attach to the pump 16. Accordingly, a vacuum (e.g., suction) may be drawn through fluid collection device 12 via the urine collection container 14. Fluid, such as urine, may be drained from the fluid collection device 12 using the pump 16.

The pump 16 or vacuum source may include one or more of a manual vacuum pump, and electric vacuum pump, a diaphragm pump, a centrifugal pump, a displacement pump, a magnetically driven pump, a peristaltic pump, or any pump configured to produce a vacuum. The pump 16 may provide a vacuum or suction to remove fluid from the fluid collection device 12. In some examples, the pump 16 may be powered by one or more of a power cord (e.g., connected to a power socket), one or more batteries, or even manual power (e.g., a hand operated vacuum pump). In some examples, the pump 16 may be sized and shaped to fit outside of, on, or within the fluid collection device 12. For example, the pump 16 may include one or more miniaturized pumps or one or more micro pumps. The vacuum sources disclosed herein may include one or more of a switch, a button, a plug, a remote, or any other device suitable to activate the pump 16.

Figure 5:
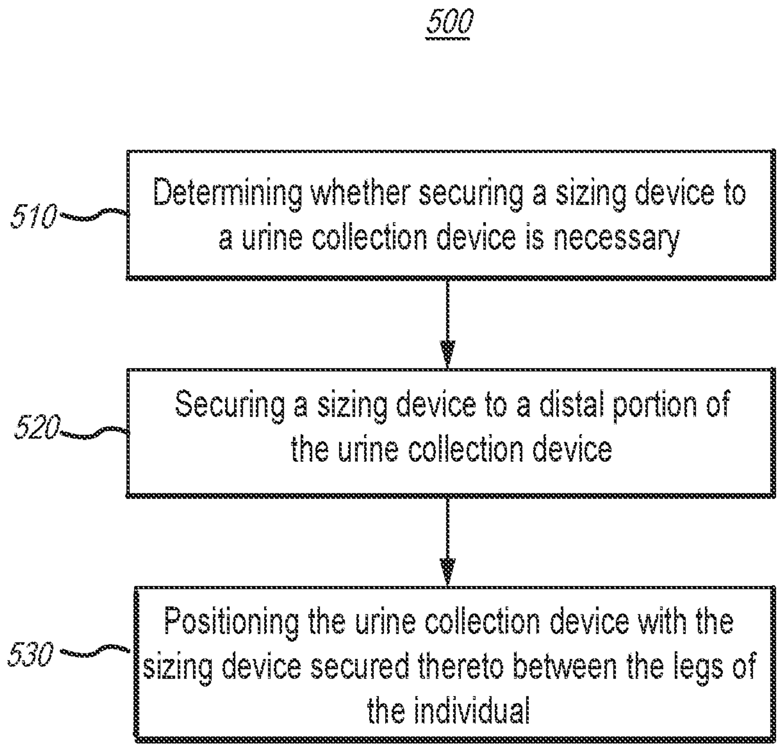
FIG. 5 is a flow diagram of a method for positioning a urine collection device on an individual, according to an embodiment.

FIG. 5 is a flow diagram of a method 500 of positioning a urine collection system on an individual. The method 500 may include an act of positioning a urine collection device between legs of the individual. The urine collection device may include any of the urine collection devices described or incorporated by reference herein, such as the urine collection device 102. In some embodiments, the method 500 may not include positioning a urine collection device between legs of the individual before determining whether a sizing device is require to stabilize the urine collection device between the legs of the individual.

The method 500 may include an act 510 determining whether securing a sizing device to the urine collection device will improve securement of the urine collection device between the legs of the individual. The sizing device may include any of the sizing devices described herein, such as sizing device 100, 200, or 300. In some embodiments, the act 510 of determining whether securing a sizing device to the urine collection device will improve securement of the urine collection device between the legs of the individual includes determining whether securing a sizing device to the urine collection device to lengthen the urine collection device will improve securement of the urine collection device between the legs of the individual. In some embodiments, the act 510 of determining whether securing a sizing device to the urine collection device will improve securement of the urine collection device between the legs of the individual includes determining whether securing a sizing device to the urine collection device to widen the urine collection device will improve securement of the urine collection device between the legs of the individual. In some embodiments, the act 510 of determining whether securing a sizing device to the urine collection device will improve securement of the urine collection device between the legs of the individual includes positioning different sizing devices between the legs of the individual to identify a sizing device that interfaces or contacts the legs or gluteal cleft of the individual effective to remain in place between the legs of the individual when the individual is laying down.

The method 500 also may include an act 520 of securing the sizing device to a distal portion of the urine collection device. In some embodiments, the act 520 of securing the sizing device to a distal portion of the urine collection device includes inserting the distal portion of the urine collection device into a recess in the sizing device. The method also may include an act 530 of positioning the urine collection device with the sizing device secured thereto between the legs of the individual.

The acts of the method 500 described above are for illustrative purposes. For example, the acts of the method 500 can be performed in different orders, split into multiple acts, modified, supplemented, or combined. In an embodiment, one or more of the acts of the method 500 can be omitted from the method 500. Any of the acts of the method 500 can include using any of the urine collection systems disclosed herein.

As used herein, the term “about” or “substantially” refers to an allowable variance of the term modified by “about” or “substantially” by ±10% or ±5%. Further, the terms “less than,” “or less,” “greater than,” “more than,” or “or more” include, as an endpoint, the value that is modified by the terms “less than,” “or less,” “greater than,” “more than,” or “or more.”

While various aspects and embodiments have been disclosed herein, other aspects and embodiments are contemplated. The various aspects and embodiments disclosed herein are for purposes of illustration and are not intended to be limiting.

What is claimed is:

1. A urine collection system, comprising:

a urine collection device including a fluid impermeable barrier having a proximal end portion and a closed distal end portion, the fluid impermeable barrier defining an opening between the proximal end portion and the closed distal end portion, an aperture in the proximal end portion, and a chamber in fluid communication with the opening and at least partially defined by the closed distal end portion, the urine collection device further including a fluid permeable support extending across at least a portion of the opening and a conduit in fluid communication with the chamber and configured to pull fluid held in the chamber defined at least partially by the closed distal end portion from the chamber when a suction force is applied to the conduit; and a sizing device secured or securable to the urine collection device, the sizing device including:

a body having a distal end and an attachment end spaced from the distal end, the attachment end defining an opening; and an inner surface defining a recess extending into the body from the opening, the recess being sized and dimensioned to receive the closed distal end portion of the urine collection device and selectively secure the sizing device to the urine collection device with a friction fit between the closed distal end portion and at least a portion of the inner surface of the sizing device, wherein the body is sized and dimensioned to interface and/or contact legs and/or a gluteal cleft of a user when the sizing device is secured to the urine collection device.

2. The urine collection system of claim 1, wherein:

the closed distal end portion of the urine collection device includes a substantially cylindrical region; and the recess of the sizing device includes a substantially cylindrical portion sized and dimensioned to receive at least a portion of the closed distal end portion of the urine collection device and secure the sizing device to the urine collection device, the substantially cylindrical portion having a width substantially equal to a width of the closed distal end portion of the fluid impermeable barrier effective to friction fit the substantially cylindrical region of the closed distal end portion in the substantially cylindrical portion of the recess.

3. The urine collection system of claim 2, wherein the recess of the sizing device is shaped complementary to the closed distal end portion of the urine collection device.

4. The urine collection system of claim 2, wherein the closed distal end portion includes the substantially cylindrical region and a substantially semispherical region and the recess of the sizing device includes the substantially cylindrical portion and a substantially semispherical portion sized and dimensioned complementary to the substantially cylindrical region and the substantially semispherical portion of the fluid impermeable barrier effective to friction fit the closed distal end portion within the recess.

5. The urine collection system of claim 1, wherein the body of the sizing device includes a substantially cylindrical portion positioned between the attachment end and the distal end.

6. The urine collection system of claim 5, wherein the sizing device includes a substantially frustoconical head tapering at least partially between the cylindrical portion and the attachment end.

7. The urine collection system of claim 5, wherein the sizing device includes a semispherical base tapering at least partially between the cylindrical portion and the distal end.

8. The urine collection system of claim 5, wherein the body of the sizing device includes a length from the distal end to the attachment end of at least 5 cm and a maximum width of at least about 3.75 cm.

9. The urine collection system of claim 5, wherein the sizing device includes an elongated frustoconical base tapering at least partially between the cylindrical portion and the distal end.

10. The urine collection system of claim 9, wherein the elongated frustoconical base is at least about 3.75 cm.

11. The urine collection system of claim 9, wherein the body includes a length from the distal end to the attachment end of at least 6.25 cm and a maximum width of at least about 2.5 cm.

12. The urine collection system of claim 1, wherein the body includes a generally ellipsoid shape.

13. The urine collection system of claim 12, wherein the body includes a maximum width of at least 6.25 cm.

14. The urine collection system of claim 12, wherein the body includes a length of about 2.5 cm to about 5 cm.

15. The urine collection system of claim 1, wherein the opening includes a diameter of about 1.75 cm to about 3.25 cm.

16. The urine collection system of claim 1, wherein the recess includes a depth of about 1.25 cm to about 2.5 cm.

17. A method of positioning a urine collection system on an individual, the method comprising:

positioning a urine collection device between legs of the individual, the urine collection device including a fluid impermeable barrier having a proximal end portion and a closed distal end portion, the fluid impermeable barrier defining an opening between the proximal end portion and the closed distal end portion, an aperture in the proximal end portion, and a chamber in fluid communication with the opening and at least partially defined by the closed distal end portion, the urine collection device further including a fluid permeable support extending across at least a portion of the opening and a conduit in fluid communication with the chamber and configured to pull fluid held in the chamber defined at least partially by the closed distal end portion from the chamber when a suction force is applied to the conduit;

determining whether securing a sizing device to the urine collection device will improve securement of the urine collection device between the legs of the individual, the sizing device including:

a body having a distal end and an attachment end spaced from the distal end, the attachment end defining an opening; and an inner surface defining a recess extending into the body from the opening, the recess being sized and dimensioned to receive the closed distal end portion of the urine collection device and selectively secure the sizing device to the urine collection device with a friction fit between the closed distal end portion and at least a portion of the inner surface of the sizing device;

securing the sizing device to closed distal end portion of the urine collection device; and positioning the urine collection device with the sizing device secured thereto between the legs of the individual with the body interfacing and/or contacting the legs and/or gluteal cleft of the individual.

18. The method of claim 17, wherein securing the sizing device to a closed distal end portion of the urine collection device includes inserting the closed distal end portion of the urine collection device into the recess in the sizing device.

19. The method of claim 17, wherein determining whether securing a sizing device to the urine collection device will improve securement of the urine collection device between the legs of the individual includes determining whether securing a sizing device to the urine collection device to lengthen the urine collection device will improve securement of the urine collection device between the legs of the individual.

20. The method of claim 17, wherein determining whether securing a sizing device to the urine collection device will improve securement of the urine collection device between the legs of the individual includes determining whether securing a sizing device to the urine collection device to widen the urine collection device will improve securement of the urine collection device between the legs of the individual.

* * * * *